(12) United States Patent
Paluh et al.

(10) Patent No.: US 9,567,380 B1
(45) Date of Patent: Feb. 14, 2017

(54) MICROTUBULE ORGANIZING CENTER (MTOC)-INACTIVATING PEPTIDES

(71) Applicant: THE RESEARCH FOUNDATION FOR THE STATE UNIVERSITY OF NEW YORK, Albany, NY (US)

(72) Inventors: Janet L. Paluh, Malta, NY (US); Zachary T. Olmsted, Oneida, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 14/925,577

(22) Filed: Oct. 28, 2015

(51) Int. Cl.
*A61K 38/46* (2006.01)
*C07K 14/39* (2006.01)
*C12N 9/14* (2006.01)
*C12Q 1/34* (2006.01)
*G01N 33/50* (2006.01)

(52) U.S. Cl.
CPC .............. *C07K 14/39* (2013.01); *A61K 38/46* (2013.01); *C12N 9/14* (2013.01); *C12Q 1/34* (2013.01); *G01N 33/5011* (2013.01); *C12Y 306/01003* (2013.01)

(58) Field of Classification Search
CPC ..................................................... A61K 38/46
See application file for complete search history.

(56) References Cited

PUBLICATIONS

Olmsted et al (Nature Communications: pp. 1-15, published Oct. 28, 2014).*

* cited by examiner

*Primary Examiner* — Catherine S Hibbert
(74) *Attorney, Agent, or Firm* — Heslin Rothenberg Farley and Mesiti, PC; Kathy Smith Dias

(57) ABSTRACT

Disclosed herein is the identification of a new therapeutic target, an upstream target, the microtubule-organizing center (MTOC), for arresting mitosis and inhibiting cell growth and proliferation. Achieving mitotic arrest involves the interaction of two proteins with the γTuRC of the MTOC: Kinesin-14 or a Tail peptide of Kinesin-14 having the amino acid sequence of SEQ ID NO: 1 and an antagonist capable of disarming the function of the BimC domain of Kinesin-5. Methods and compositions for screening for Kinesin-5 BimC antagonists are also disclosed.

5 Claims, 45 Drawing Sheets
(27 of 45 Drawing Sheet(s) Filed in Color)

Spindle MT Density in Anaphase B wild type    pkl1Δ cut7Δ

SPB    Type 1   Type 2   Type 3

SPB

Fig. 9E

SEQUENCE LISTING

```
<160> NUMBER OF SEQ ID NOS: 9

<210> SEQ ID NO 1
<211> LENGTH: 31
<212> TYPE: PRT
<213> ORGANISM: Artificial Sequence
<220> FEATURE:
<223> OTHER INFORMATION: synthetic peptide

<400> SEQUENCE: 1

Tyr Ser Lys Phe Lys Glu Ser Ala Ala Pro Gln Leu Lys Asp Leu Ile
1               5                   10                  15

Gly Ser Gly Ala Glu Lys Asp His Glu Tyr Ser Leu Gln Leu Gln
            20                  25                  30

<210> SEQ ID NO 2
<211> LENGTH: 25
<212> TYPE: PRT
<213> ORGANISM: Artificial Sequence
<220> FEATURE:
<223> OTHER INFORMATION: synthetic peptide
```

```
<400> SEQUENCE: 2

His His His His His His Tyr Ser Lys Phe Lys Glu Ser Trp Leu Pro
1               5                   10                  15

Gln Leu Lys Asp Leu Ile Glu Ser His
            20                  25

<210> SEQ ID NO 3
<211> LENGTH: 25
<212> TYPE: PRT
<213> ORGANISM: Artificial Sequence
<220> FEATURE:
<223> OTHER INFORMATION: synthetic peptide

<400> SEQUENCE: 3

His His His His His His Tyr Ser Lys Phe Lys Glu Ser Ala Ala Pro
1               5                   10                  15

Gln Leu Lys Asp Leu Ile Gly Ser Gly
            20                  25

<210> SEQ ID NO 4
<211> LENGTH: 37
<212> TYPE: PRT
<213> ORGANISM: Artificial Sequence
<220> FEATURE:
<223> OTHER INFORMATION: synthetic peptide

<400> SEQUENCE: 4

His His His His His His Tyr Ser Lys Phe Lys Glu Ser Ala Ala Pro
1               5                   10                  15

Gln Leu Lys Asp Leu Ile Gly Ser Gly Ala Glu Lys Asp His Glu Tyr
            20                  25                  30

Ser Leu Gln Leu Gln
        35

<210> SEQ ID NO 5
<211> LENGTH: 230
<212> TYPE: PRT
<213> ORGANISM: Schizosaccharomyces pombe

<400> SEQUENCE: 5

Met Val Ile Glu Asn Thr Lys Asp Ile Ser Ile Asn Thr Gly Tyr Lys
1               5                   10                  15

Arg Gln Glu Asp Ala Leu Asn Thr Asp Ser Glu Asp Leu Ile Tyr Arg
            20                  25                  30

Pro Lys Lys Ile Ile Lys Thr Asn Gln Glu Asp Ala Val His Asp Leu
        35                  40                  45

Lys Tyr Glu Asn Phe Val Ser Lys Asn His Val Leu Gln Ser Asp Ile
    50                  55                  60

Asn Gly Lys Lys Arg Asp Ser Asn Arg Asp Lys Ala Ala Val Val Thr
65                  70                  75                  80

Ala Pro Ile Ala Ser Thr His Glu Ser Asn Tyr Glu Glu Ser Val Ser
                85                  90                  95

Lys Phe Lys Glu Ser Trp Leu Pro Gln Leu Asp Leu Ile Glu Ser
            100                 105                 110

His Lys Thr Ile Cys Glu Ser Thr Leu Ala Tyr Glu Ser Asp Gln Ala
        115                 120                 125

Met Ala Ser Ser Asn Thr Leu Lys Arg Ile Lys Asp Leu Lys Ser Lys
    130                 135                 140

Pro Lys Asn Ile Ile Gln Leu Glu Arg Leu His Met Leu Ser Asn Gly
```

```
                145                 150                 155                 160
Glu His Arg Leu Leu Ser Lys Asp Glu Thr Asp Ile Glu Ser Ala
                    165                 170                 175
Tyr Leu Asn Leu Arg Ser His Leu Gln Val Gln Glu Gln Val Tyr Ala
                180                 185                 190
Glu Lys Asp His Glu Tyr Ser Leu Gln Leu Gln Ser Tyr Arg Glu Ala
            195                 200                 205
Ala Glu Lys Ala Lys Gln Asp Ile Leu Glu Thr Lys Glu Asn Leu Ser
        210                 215                 220
Ser Glu Leu Ser Ile Ser
225                 230

<210> SEQ ID NO 6
<211> LENGTH: 17
<212> TYPE: PRT
<213> ORGANISM: Artificial Sequence
<220> FEATURE:
<223> OTHER INFORMATION: synthetic peptide

<400> SEQUENCE: 6

Tyr Thr Gly Asp Thr Pro Ser Lys Arg Glu Leu Pro Ala Thr Pro Ser
1               5                   10                  15
Trp

<210> SEQ ID NO 7
<211> LENGTH: 23
<212> TYPE: PRT
<213> ORGANISM: Artificial Sequence
<220> FEATURE:
<223> OTHER INFORMATION: synthetic peptide

<400> SEQUENCE: 7

His His His His His His Tyr Thr Gly Asp Thr Pro Ser Lys Arg Glu
1               5                   10                  15
Leu Pro Ala Thr Pro Ser Trp
            20

<210> SEQ ID NO 8
<211> LENGTH: 23
<212> TYPE: PRT
<213> ORGANISM: Artificial Sequence
<220> FEATURE:
<223> OTHER INFORMATION: synthetic peptide

<400> SEQUENCE: 8

His His His His His His Tyr Thr Gly Asp Thr Pro Ser Lys Arg Glu
1               5                   10                  15
Leu Pro Ala Asp Pro Ser Trp
            20

<210> SEQ ID NO 9
<211> LENGTH: 23
<212> TYPE: PRT
<213> ORGANISM: Artificial Sequence
<220> FEATURE:
<223> OTHER INFORMATION: synthetic peptide
```

```
<400> SEQUENCE: 9

His His His His His His Tyr Thr Gly Asp Thr Pro Ser Lys Arg Glu
1               5                   10                  15

Leu Pro Ala Thr Ser Ser Trp
            20
```

MICROTUBULE ORGANIZING CENTER (MTOC)-INACTIVATING PEPTIDES

SEQUENCE LISTING

This application contains a Sequence Listing, created on Oct. 21, 2015; the file, in ASCII format, is designated 2835135_ST25.txt and is 4.84 KB in size. The file is hereby incorporated by reference in its entirety into the present disclosure.

TECHNICAL FIELD

The present invention relates generally to anti-mitotic agents and in particular to methods and compositions for improved anti-mitotic efficacy of drugs by targeting the microtubule-organizing center (MTOC).

BACKGROUND OF THE INVENTION

Cancer is a ubiquitous disease of unregulated cell proliferation that can lead to tumor formation and systemic metastatic seeding of cancerous growth at new physical sites. In all cancers, the targeting of microtubule spindle assembly has been shown to be an effective anti-proliferative therapy and enhances patient survival giving rise to perhaps the most potent class of anti-cancer therapeutic drugs available: those that lead to genomic instability and growth arrest by targeting the mitotic spindle, which is crucial for genetic fidelity during cell division. Mitotic spindle protein (MSP) drugs that have been developed for cancers include those that target the dynamic behavior of the microtubules (such as paclitaxel) or the bipolar organization of microtubules such as blocking microtubule binding of the Kinesin-5 motor domain (for example, Ispinisib or Monastrol.)

Anti-MSPs are proven, powerful anti-cancer reagents, yet the current portfolio of MSP drugs approved or in the pipeline is insufficient in terms of the structural and functional complexity of the mitotic spindle. What is needed, therefore, are agents with the ability to act upstream of other anti-MSP cancer therapies, which would eliminate cancer cell access to typical mitotic recovery mechanisms and reduce or block drug resistant lines from developing, either alone or in combination with other anti-MSPs.

SUMMARY OF THE INVENTION

The disclosure describes the MTOC as a newly identified upstream target for arresting mitosis and inhibiting cell growth and proliferation. The disclosure provides methods and compositions for upstream interruption of mitosis that function by blocking spindle formation in the first instance rather than allowing a spindle to form and subsequently blocking its function(s). Two proteins, Kinesin-14 and Kinesin-5, are involved. Kinesin-14 blocks microtubule nucleation and Kinesin-5 counters the Kinesin-14 block of MTOC nucleation, allowing nucleation to continue. By blocking the BimC domain of Kinesin-5, the ability of kinesin-5 to drive MTOC nucleation is removed.

In one aspect, the disclosure relates to a synthetic peptide comprising the amino acid sequence of SEQ ID NO: 6 that functions as an antagonist of Kinesin-5 BimC domain.

In one aspect, the disclosure relates to a method for induction of mitotic arrest and growth inhibition in cells, the method comprising contacting said cells with a Kinesin-14 tail peptide comprising the amino acid sequence of SEQ ID NO: 1 and a Kinesin-5 antagonist that blocks the BimC domain of Kinesin-5, thereby preventing Kinesin-5 from countering the ability of Kinesin-14 to block MTOC nucleation. The method is applicable to eukaryotic cells, mammalian cells, including human breast cancer cells.

In a related aspect, the disclosure relates to a composition comprising a Kinesin-14 tail peptide consisting of the amino acid sequence of SEQ ID NO: 1 and a Kinesin-5 antagonist that blocks BimC domain of Kinesin-5.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 9A-G show that spindle breakdown is delayed in the pkl1Δ cut7Δ double mutant. (A-C) Timelapse fluorescence microscopy of persistent anaphase B spindles in double mutant cells. Three types of spindle microtubule density were observed, shown in (E). (D) Mitotic index versus time for wild type (black curve), pkl1Δ (dark grey curve) and pkl1Δ cut7Δ cells (light grey curve) following hydroxyurea arrest and release. Spindle length was measured using microtubule stain by ICC. (E) Schematic of three types of anaphase spindle microtubule density observed in pkl1Δ cut7Δ double mutant cells. (F) Stacked histogram representation of spindle microtubule density phenotypes across strains. n=300 cells averaged over three time points per strain. (G) Kymographs of a wild type spindle (top; yellow arrow indicates spindle breakdown) and a persistent spindle (red arrow) shown from the time series for Type 3. All scale bars are 5 μm.

DETAILED DESCRIPTION OF THE INVENTION

Figure 1A:
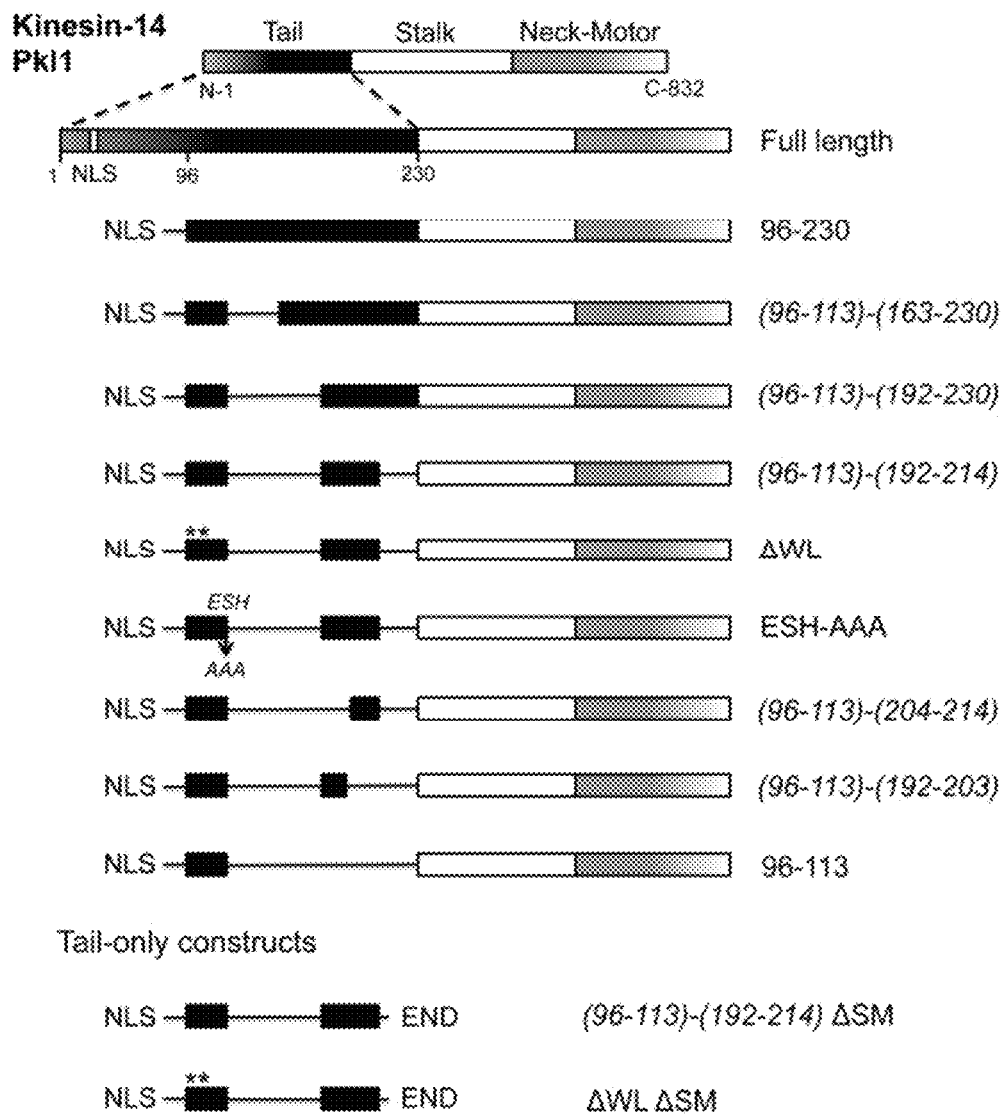
FIGS. 1A-D show that two domains in kinesin-14 Pkl1 regulate bipolar spindle assembly. (A) Diagram of full-length Plk1 showing domains. Tail constructs are derived from starting construct 96-230 as shown. Amino acid regions 1-95, 114-191 and 204-230 are dispensable for function in our assays. Two Tail-only derivatives were also generated and are expanded on in FIG. 2. The 10 aa nuclear localization signal (NLS) sequence is deleted in amino acids 1-95 and must be fused to each construct for nuclear entry. (B) Representative images (n>3) of serial dilution growth assays for monitoring Pkl1 function in the presence of altered Tail domain elements. Note, these constructs contain the unaltered Pkl1 Stalk, Neck and Motor domains. Gradient bars indicate increasing dilutions of cells. Functional Pkl1 inhibits growth at 36° C. (D) Spindle localization of GFP-Pkl1 fusion proteins with modified Tail regions. Tail derivatives shown in (D) are functional, whereas Tail derivatives (not shown) are non-functional based on serial dilution growth assays in (C). Therefore, spindle pole targeting is necessary but not sufficient for function. Representative images from n=200. Scale bar is 5 microns.

All patents, applications, publications and other references listed herein are hereby incorporated by reference in their entirety.

In practicing the presently disclosed methods, many conventional techniques in molecular biology, microbiology, cell biology, biochemistry, and immunology are used, which are within the skill of the art. These techniques are described in greater detail in, for example, Molecular Cloning: a Laboratory Manual 3rd edition, J. F. Sambrook and D. W. Russell, ed. Cold Spring Harbor Laboratory Press 2001; "Current Protocols in Molecular Biology" (F. M. Ausubel et al., eds., 1987, and periodic updates). The contents of these references and other references containing standard protocols, widely known to and relied upon by those of skill in the art, including manufacturers' instructions are hereby incorporated by reference as part of the present disclosure.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

ABBREVIATIONS

γ-TuSC: γ-tubulin small complex
γ-TuRC: γ-tubulin ring complex
MTOC: microtubule-organizing center
MT: microtubule(s)
Klp: kinesin-like protein
SPB: spindle pole body The term "ortholog" refers to genes in different species that are similar in their nucleotide sequences, suggesting that they originated from a common ancestral gene.

The term "peptide" as it is known in the art refers to a molecule comprising two or more amino acids, generally fewer than fifty, where the alpha-carboxylic group of one is bound to the alpha-amino group of the other. Because of their relatively small size, the peptides of the disclosure may be directly synthesized in solution or on a solid support in accordance with conventional peptide synthesis techniques. Various automatic synthesizers are commercially available and can be used in accordance with known protocols. The synthesis of peptides in solution phase has become a well-established procedure for large-scale production of synthetic peptides and as such is a suitable alternative method for preparing the peptides of the invention. (See for example, Solid Phase Peptide Synthesis by John Morrow Stewart and Martin et al. Application of Almez-mediated Amidation Reactions to Solution Phase Peptide Synthesis, Tetrahedron Letters Vol. 39, pages 1517-1520 1998.)

Short peptide sequences, or libraries of overlapping peptides which correspond to the selected regions described herein, can be readily synthesized and then screened in assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression. Methods for production of a peptide by recombinant DNA technology are well known to those of skill in the art.

In all eukaryotes, a designated macromolecular complex termed the microtubule-organizing center (MTOC) serves a fundamental role in the initial formation of microtubules (nucleation) as well as their organization, dynamics and temporal cell cycle changes in these parameters once formed. The γ-tubulin ring complex (γ-TuRC) is the core functional unit of the MTOC across eukaryotes and controls spindle assembly by directly controlling microtubule nucleation (the presence of microtubules). A unique fission yeast Kinesin-14 molecular motor protein, Pkl1, is one of few proteins known to function in spindle assembly by directly interacting with the γ-TuRC to alter its structure and block its functional ability to grow microtubules.

Bipolar spindle assembly is a critical control point for initiation of mitosis through nucleation and organization of spindle microtubules and is regulated by Kinesin-like proteins. In fission yeast, the Kinesin-14 Pkl1 binds the γ-tubulin ring complex (γ-TuRC) microtubule-organizing center at spindle poles and can alter its structure and function. Here we show that Kinesin-14 blocks microtubule nucleation in yeast, and reveal that this inhibition is countered by the Kinesin-5 protein, Cut7, when it binds to γ-TuRC (Olmsted et al. Nat Communications 2014). We demonstrate that Cut7 binding to γ-TuRC and in particular the Cut7 BimC domain are both required for inhibition of Pkl1. We also demonstrate that a yeast Kinesin-14 peptide biochemically removes γ-tubulin from the human γ-TuRC similar to the yeast mechanism. Furthermore that a Kinesin-14 peptide blocks microtubule nucleation in vivo in two human breast cancer cell lines, suggesting that this mechanism is evolutionarily conserved.

The microtubule cytoskeleton is a self-assembling network that underlies specialized, often polarized, cellular functions in eukaryotes. Knowledge of its mechanisms is fundamental to understanding normal development and disease and is expected to assist new technologies through biomimicry. The microtubule-based mitotic spindle apparatus is perhaps the best studied self-assembly platform[1,2] and a primary target for cancer therapeutics[3]. Spindle pole microtubule-organizing centers (MTOCs) utilize a γ-tubulin template within a ring complex (γ-tubulin ring complex, γ-TuRC) to orchestrate addition of α-/β-tubulin heterodimeric microtubule building blocks into 25 nm polarized microtubules[4-9]. Conserved protein structural features of the γ-TuRC MTOC have been identified through crystallography studies from multiple model organisms and include α-/β-tubulin[10], γ-tubulin[11], GCP4[12] and the γ-tubulin small complex (γ-TuSC) cryo-EM structure[13]. Conserved structural features are additionally supported by cross-species analysis[14,15]. Still unknown is how dynamic control over MTOC functions for microtubule nucleation and organization is achieved. The fission yeast *Schizosaccharomyces pombe* provides an ideal eukaryotic platform to address conserved MTOC mechanisms[14-17].

The coordination of spindle microtubules into a bipolar array requires Kinesin-like proteins (Klps), though Klp mitotic functions are not limited to interactions solely on microtubules. Studies of the functionally diverse Kinesin-14 Klp family across eukaryotes have indicated an ability by some members to affect microtubule number and organization at spindle poles[18-21]. In fission yeast, Kinesin-14 Pkl1 interacts directly with the γ-TuRC MTOC to alter its composition and function[17,22,23]. Conservation of the Kinesin-14 γ-TuRC regulatory mechanism is expected from yeast to human since human Kinesin-14 HSET replaces fission yeast Kinesin-14 Pkl1[23] and all human γ-TuSC protein components are also compatible[14,18]. Nearly as ubiquitous and complex in eukaryotes as Kinesin-14 Klps are members of the Kinesin-5 family that oppose Kinesin-14 function. In fission yeast, Kinesin-5 Cut7 opposes the action of Kinesin-14 Pkl1 in mitosis, but the detailed mechanism is not yet characterized. Elucidating this mechanism could be informative for understanding γ-TuRC regulation and spindle bipolarity.

In this disclosure, the mechanism for Kinesin-14 regulation of γ-TuRC is described. Studies describe genetic interactions of Pkl1 with γ-TuRC proteins[22,24-26], checkpoint pathways[20,26] and spindle pole organization[20]. More recently key Tail elements in Pkl1 that function along with Motor binding to γ-tubulin to regulate γ-TuRC[17,22-23] were identified. The present disclosure demonstrates that Kinesin-14 Pkl1 asymmetrically blocks microtubule nucleation in vivo in fission yeast and that a Kinesin-14 Pkl1 Tail peptide can similarly prevent nucleation and generate mitotic arrest in two human breast cancer cell lines. In fission yeast, Kinesin-5 Cut7 counters Pkl1 ability to block nucleation by also associating with γ-TuRC and binding similarly to γ-tubulin. This counter-action requires the additional conserved Kinesin-5 BimC domain. Balanced regulation by Kinesin-14 Pkl1 and Kinesin-5 Cut7 generates optimal mitotic fidelity, although both proteins are co-dispensable as determined by genetic analysis of single and double mutants, biochemical approaches and timelapse fluorescence microscopy.

Analysis of pkl1Δ single and pkl1Δ cut7Δ double mutants also reveals separate mitotic roles for Kinesin-14 Pkl1 and Kinesin-5 Cut7. These findings identify Kinesin-14 Pkl1 as a Klp negative regulator of microtubule nucleation at γ-TuRC and demonstrate conservation of this mechanism in human breast cancer cells, resulting in mitotic arrest. Furthermore these findings indicate that a primary role of Cut7 is to counter Pkl1 and allow microtubule nucleation for spindle assembly.

Microtubule organizing centers play major roles in specialized eukaryotic processes of broad interest such as spindle assembly, neuronal function and immunological synapse formation that involves cell polarization. Understanding the detailed mechanisms for microtubule nucleation requires combined knowledge of the underlying structure along with regulatory insights. This work demonstrates that the ability of fission yeast Kinesin-14 Pkl1 to bind and alter γ-TuRC structure and function[17] results in blocked microtubule nucleation in vivo generating failed spindle bipolarity and mitotic arrest. Conservation of this mechanism is revealed through use of a Kinesin-14 Pkl1 peptide PγTR in human breast cancer cells that localizes to centrosomes and is sufficient to arrest nucleation in the two breast cancer cell lines investigated, representing low and highly aggressive grades, by preventing bipolar spindle formation. In fission yeast, Kinesin-5 Cut7 but not Kinesin-14 Pkl1, is an essential mitotic protein[18,27]. To better understand Kinesin-14 Pkl1 function at γ-TuRC, and Kinesin-5 counter-action of this Klp, we applied genetic analysis, biochemistry and timelapse imaging. Here we show that Kinesin-5 Cut7 is dispensable in the absence of Kinesin-14 Pkl1 and that counter-action of Pkl1 by Cut7 requires Cut7 binding to γ-TuRC through its Motor and BimC domains. These Klps are the first identified to directly bind and regulate γ-TuRC, actions that are sufficient to impact microtubule nucleation capability. These findings are expected to have significant impact in the cytoskeleton field, particularly in understanding MTOC function as well as in potential therapeutic anti-cancer applications that utilize mitotic spindle protein antagonists.

Distinct mitotic phenotypes are present with loss of either Pkl1 or Cut7. The loss of pkl1 in the presence of cut7, although viable, results in an asymmetric effect on daughter spindle pole organization that influences spindle width and impairs chromosome segregation. Compared to the double mutant pkl1Δcut7Δ, no amelioration or exacerbation of the pkl1Δ phenotype is observed, indicating that these phenotypes are likely due to loss of Pkl1. The additional loss of Cut7, however, does result in delayed spindle breakdown for mitotic exit. Cut7 localizes to the spindle midzone in anaphase[37], and although not required for anaphase B spindle elongation[29], our data indicate it may contribute to normal progression through this stage. A primary role for Kinesin-5 Cut7 is therefore to counter-act Kinesin-14 Pkl1 at γ-TuRC. Only in the presence of Pkl1 does removal of Cut7 or inactivation of the Cut7 BimC domain (cut7-22) allow an asymmetric block on γ-TuRC microtubule nucleation to be imposed that results in failed spindle bipolarity (FIG. 8).

Extensive studies demonstrate both the importance of Kinesin-5 motors in spindle assembly along with Kinesin-5 independent mechanisms. In the latter, force generation by other microtubule motors such as nuclear envelope-associated dynein and Kinesin-12 operate and include microtubule pushing forces on the opposing pole and kinetochore-mediated microtubule interactions in prophase[38]. Our ability to remove Kinesin-5 Cut7 in the absence of Kinesin-14 Pkl1 reveals that in fission yeast Kinesin-5 independent mechanisms exist to establish spindle bipolarity.

Spindle phenotypes in the double mutant and single pkl1Δ strains do not include changes to timing for prophase SPB separation or mitotic progression through anaphase B versus wild type. The increase in spindle thickness upon loss of Pkl1 is reminiscent of phenotypes induced by loss of Kinesin-14 Kar3 in budding yeast[19]. The thick spindle morphology did not result in increased resistance to the microtubule-depolymerizing drug TBZ at 10 or 20 μg/mL concentrations in single or double mutant backgrounds versus wild type, consistent with no change in spindle microtubule number. We favor the model that altered microtubule organization of parallel microtubules emanating from the daughter pole results in increased spindle width at this pole as opposed to an increase in spindle microtubule number. This is consistent with studies by ref. 20 in which TEM analysis of pkl1Δ cells revealed a decrease in pole organization characterized by loss of the typical plaque-like structure with apparent normal microtubule number. The replication of the spindle pole body and centrosome are semi-conservative with the mother pole used as a template. In order to identify whether the mother or daughter pole is affected by loss of pkl1 we applied live cell fluorescence microscopy with asymmetric pole markers Cdc7-GFP and Mad2-GFP along with mCherry-Atb2 to mark microtubules. Our studies reveal that the daughter pole is affected in both pkl1Δ single mutant and pkl1Δ cut7Δ double mutant cells. Daughter pole disorganization additionally affects cytoplasmic astral microtubule arrays. Mitotic events can influence licensing and semi-conservative centrosome replication in the succeeding G1/S. In human cells, separase and polo kinase license centrosomes for duplication in the next cell cycle during mitosis[39]. Whether loss of Kinesin-14 Pkl1 impacts subsequent cell cycle events outside of mitosis is not known. However, the changes to daughter spindle pole integrity without Pkl1 indicate a broader role beyond microtubule nucleation for spindle assembly, such as maturation or integrity of the daughter MTOC. We did not detect a similar role with Kinesin-5 at the daughter MTOC and additional loss of Cut7 does not exacerbate these phenotypes. The concept of asymmetric events at spindle poles is well known. In budding yeast, γ-tubulin mutants have been isolated that block robust microtubule nucleation from a single pole as seen by transmission electron microscopy[40]. In human cells, mother centriole stability is asymmetrically affected by Kinesin-13 Kif24[41]. As well, regulation of poles can be asymmetric and is observed in mitotic checkpoint pathways[26,34,35,42-47] that monitor spindle assembly, positioning and timing to help ensure the accurate segregation of chromosomes in cell division.

This study demonstrates that the role of Kinesin-14 at γ-TuRC is to block microtubule nucleation and that key domains are required for this mechanism. This ability to localize to γ-TuRC at spindle pole bodies is conserved with γ-TuRC in the mammalian centrosome. We additionally identified the ability of Kinesin-5 to bind γ-TuRC as a key component in the Klp/γ-TuRC regulatory mechanism in fission yeast. Pkl1 interacts with γ-TuRC through two domains, a Motor domain that binds to γ-tubulin helix 11 and distinct Tail domain binding to the complex. The combined domains provide strongest interactions with γ-TuRC[17]. Data indicates that similar to Pkl1, the Tail domain of Cut7 is the primary γ-TuRC targeting element. We hypothesize that the Motor domain plays a role in assisted targeting to the γ-TuRC site at spindle poles and in competition with Pkl1 binding to this site. Consistent with our previously published findings on Pkl1, we observe that the combined domains of Cut7 provide the strongest interactions with γ-TuRC. However, unlike Pkl1 that has low affinity to microtubules[48], Cut7 retains the ability to bind strongly to spindle tubulins when γ-tubulin specific binding is prevented. This alternative site of interaction may lower the pool of Cut7 at γ-TuRC. Thus, as a consequence of blocked loading due to the helix 11 mutation and retained high microtubule binding affinity, we would expect reduced binding of Cut7 to γ-TuRC complexes with γ-tubulin-K5A present as compared to Cut7ST, as observed. Interestingly, the cut7-22 mutation lies within a MAP kinase phosphorylation consensus sequence in the conserved BimC sequence of the Cut7 Tail domain[29] indicating that phosphorylation at this or other kinase sites within this domain may be important in the γ-TuRC mechanism. Finally the dual regulatory relationship of Kinesin-14 and Kinesin-5 at the γ-TuRC in fission yeast, along with the ability of PγTR peptide to block nucleation and spindle bipolarity in breast cancer cells is impactful in regard to cancer therapy[49].

Our findings are of particular interest in regard to multiple clinically oriented studies[52-89] that demonstrate overexpression of γ-tubulin and other centrosomal proteins is characteristic of tumorigenesis and human malignancies in multiple tissues. In this case supernumerary microtubule-nucleating centrosomes are often observed and result in abnormal multipolar mitoses, aneuploidy and ultimately cell death[58,59,61]. Likewise, overexpression of γ-tubulin in malignant cells can also produce ectopic microtubule nucleation in the cytoplasm. This is thought to result from γ-tubulin-centrosome decoupling as well as sub-cellular sorting changes to soluble cytoplasmic pools or insoluble centrosomal complexes[52,57,58,60] as well as insoluble cytoplasmic aggregates[53]. Interestingly, an increase in the percentage of soluble cytoplasmic γ-tubulin is associated with cell lines of higher aggressiveness and poorer prognosis versus those of low or moderate aggressiveness[58]. Further, γ-tubulin can be incorporated within the α-/β-tubulin lattice of cytoplasmic microtubules that may impact drug resistance[58]. The ability of the PγTR peptide to target complexed γ-tubulin could allow a means to prevent ectopic microtubule nucleation, although currently this is untested. Regardless, the peptide can mitotically arrest both the MCF-7 low and MDA-MB-231 high aggressive cell lines with similar efficiency. The benefit of PγTR versus other anti-mitotic agents that solely target microtubules is yet to be determined but is of interest in particular for malignant cell lines that are difficult to arrest and which often develop resistance.

Combination of Kinesin-14 PγTR Peptide and Kinesin-5 Antagonist for Mitotic Arrest Presently disclosed are methods and compositions that exploit the MTOC as a therapeutic target based on the identification of two MTOC sites involved in microtubule nucleation. Accordingly, for inducing mitotic arrest and growth inhibition in cells, the methods and compositions comprise the contemporaneous use of a Kinesin-14 Tail peptide that blocks MTOC nucleation and an antagonist of the Kinesin-5 BimC domain that counters the Kinesin-14 block.

Kinesin-14 PγTR Peptide

A Kinesin-14 Tail peptide, for example the PγTR peptide, which is described in more detail in Olmsted et al. *Kinesin-14 Pkl1 targets γ-tubulin for release from the γ-tubulin ring complex (γ-TuRC)* Cell Cycle 12:5, 1-7 2013 (the contents of which are incorporated herein by reference) binds to γTuRC to block microtubule nucleation. PγTR has the following amino acid sequence:

YSKFKESAAPQLKDLIGSGAEKDHEYSLQLQ (SEQ ID NO: 1)

Identification of Kinesin-5 BimC Antagonists

Successful targeting of the MTOC to achieve mitotic arrest, however, requires more than just the action of Kinesin-14 to block nucleation. In the absence of a strategy to block the action of Kinesin-5, specifically the binding of the BimC domain of Kinesin-5 to the MTOC, the action by Kinesin-14 to prevent nucleation is itself interrupted. Accordingly, the cells are exposed not only to a Kinesin-14 Tail peptide, but also an antagonist of Kinesin-5. In one embodiment, Kinesin-5 BimC antagonists can be identified using a screening method that employs cells that express a Kinesin-14 Tail peptide, for example, PγTR peptide.

In human cancer cells, the addition of the Kinesin-14 Tail peptides blocks MT nucleation. The ability of BimC to counter Kinesin-14 removes the microtubule nucleation block. Drugs that target BimC will restore the Kinesin-14 block and can be validated using the BimC peptides.

Drug delivery of non-peptide small molecule compounds that arrest growth can be done directly on cells expressing a Kinesin-14 Tail peptide. In one embodiment, transfected human tumor cells or tumor cell lines such as breast cancer cells MCF-7 and MDA-MB-231 are prepared as described below. The cells are then cultured under conditions for cell growth in the presence and absence of potential antagonists. Cells are monitored for signs of growth arrest and/or the appearance of apoptotic cells and a compound is deemed to be a Kinesin-5 BimC antagonist when cells grown in the presence of the compound are arrested in mitosis.

In some embodiments, for example with peptides, potential antagonist/inhibitor peptides are transfected into the cells, for example in accordance with techniques well known in the art. In some embodiments, his-tags on the peptides allow identification by immunocytology. The cell proliferation assay may be done using low or high throughput platforms.

Target specificity validation: Candidate drugs are tested for BimC specificity by added increasing BimC active peptides to dilute drug activity vs BimC nonactive peptides.

Drug Screening Protocol—Yeast

In one embodiment, a protocol for identifying compounds with the ability to block BimC domain of Kinesin-5 employs yeast. Native genetic copies of both Kinesin-5 and Kinesin-14 are removed to create a double mutant (for example, in fission yeast, the cut7Δ, pkl1Δ strain described in Olmsted, Z. T. et al. Kinesin-14 Pkl1 targets γ-tubulin for release from the γ-tubulin ring complex (γ-TuRC). *Cell Cycle* 12, 842-848, 2013).

Drug delivery into cells for screening to identify non-peptide small molecule compounds that arrest growth can be done on non-spheroplasted cells in media or spheroplasted cells as necessary. For identification of peptide drugs libraries are transformed into yeast either with the use of guiding peptides (for details, see Rajerao et al. 2007) or by standard spheroplasting cells. In some embodiment, tags are included on the peptides to allow identification. The cell proliferation assay may be done in low or high throughput platforms.

Target specificity validation: Candidate drugs are validated for BimC specificity by using the BimC peptide reagents. That is using increased levels of BimC active peptides to dilute drug activity versus BimC nonactive peptide controls.

BimC Peptide Sequences

In one embodiment, a Kinesin-5 BimC peptide has the amino acid sequence: YTGDTPSKRELPATPSW (SEQ ID NO: 6) corresponding to native elements. The same sequence with an N-terminal His-tag, for example, HHHH-HHYTGDTPSKRELPATPSW (SEQ ID NO: 7) can also be used.

HisBimCP, HHHHHHYTGDTPSKRELPADPSW (SEQ ID NO: 8), is a modified BimC sequence and is always active with His-tag.

His BimC22, HHHHHHYTGDTPSKRELPATSSW (SEQ ID NO: 9), is a modified, His-tagged, BimC sequence that is inactive (control peptide).

A screening protocol is described below to identify peptide or non-peptide small molecules that 1) mimic Kinesin-14/-tubulin action or 2) block Kinesin-5/-tubulin action. The strategy can be done in yeast, human or other eukaryotic cells and will provide two new classes of drugs operating on the same mechanism.

Mimic Kinesin-14 peptide action (Active Kinesin-14 blocks MT nucleation; proliferation halted)

Block Kinesin-5 peptide action (Active Kinesin-5 allows MT nucleation; proliferation halted)

Figure 2A:
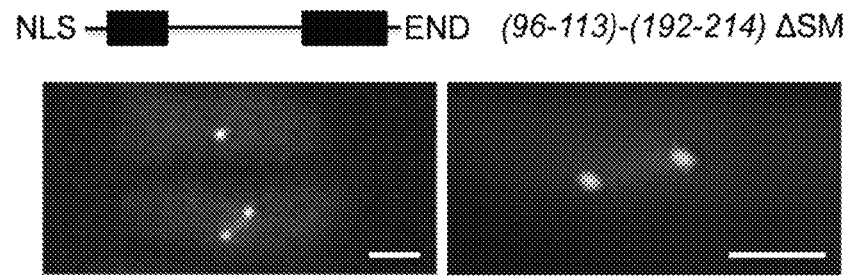
FIGS. 2A-C show that the Pkl1 Tail alone retains sufficient targeting and regulation in vivo. Critical Pkl1 Tail elements were analyzed separately from its other domains be generating Tail-only derivatives (ΔSM: delete Stalk-Motor). (A) Tail-only construct (96-113)-(192-214) ΔSM retains spindle pole targeting. Scale bar is 2 microns in both images. (B) Tail-only construct AWL is absent from poles. Scale bar is 5 microns. Asterisks mark the position of deleted residues. (C) Tail-only construct (96-113)-(192-214) ΔSM is sufficient for Pkl1 function with respect to pkl1Δ and nonfunctional AWL ΔSM in serial dilution growth assays (n>3). Gradient bars indicate increasing dilutions of cells. Growth inhibition at 36° C. indicates functional activity.
Figure 2B:
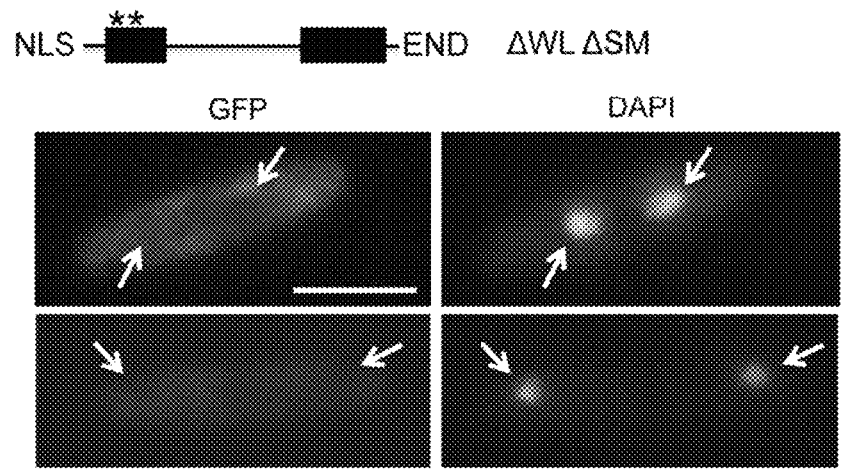
Figure 2C:
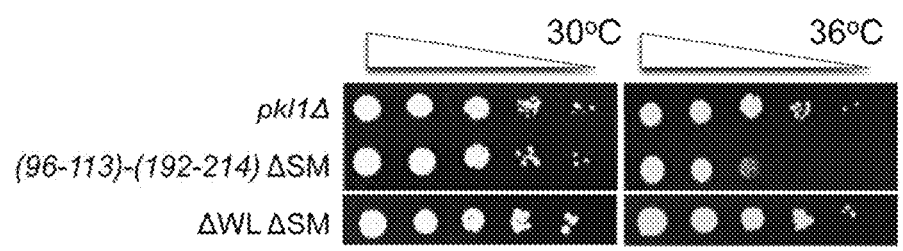

In the eukaryotic model organism fission yeast we demonstrated that active Kinesin-14 can be blocked by a fragment of the Kinesin-5 protein containing only the BimC domain (no motor-tubulin binding domain present; unpublished data, FIG. 2 BimC conserved roles).

Research in the Paluh lab has demonstrated the conservation of mechanisms between human and fission yeast for the Kinesin-14 mechanism and γ-TuSC, indicating that this yeast is an appropriate non-human model for drug screening to target conserved mechanisms of MT nucleation in mitosis for yeast, human, rat and therefore a broad range of eukaryotes (Simeonov et al. 2009; Riehlman et al. 2013; Olmsted et al. Nat Communications 2014).

EXAMPLES

Example 1

Methods

General Yeast Strains and Growth Conditions.

Standard procedures for genetic manipulation of fission yeast are as described[62] (*S. pombe* strains used are shown in Table 1). Cultures grown in fully supplemented YES rich medium or minimally supplemented medium are also as described[62]. For yeast transformations, the EZ-YEAST Transformation Kit (MP Biochemicals) was used. In growth assays, cells were grown to logarithmic phase in 10 mL rich YES media at 27° C. Cells were counted by hemocytometer and equalized and spotted at an initial concentration of $2\times10^7$ cells/mL followed by 1/10 serial dilutions. Plates incubated at 30° C. and 36° C. were grown for 4-5 days (n=3 experiments). Plates incubated at 25° C. were grown for 7 days. For promoter induction using the pREP81 low strength[63] or pREP90× high strength[64] nmt plasmids, cells were maintained on plates containing 5 μg/mL thiamine before inoculation in 10 mL selective media with (control) or without (test) 5 μg/mL thiamine for 17 hours. Plates used to assess viability contained 5 mg/L Phloxine B (Sigma-Aldrich). Mini chromosome loss was measured as described[65]. Growth curves were obtained using hemocytometer.

Site-directed mutagenesis, deletion constructs and bioinformatics. Site-directed changes or small deletions of the tail domain of the pkl1 gene were done by high-fidelity PCR with mutagenic oligonucleotides that also contained sites for cloning (Integrated DNA Technologies; Roche High Fidelity PCT Master, cat. 2140314). All constructs were sequenced (Northwoods DNA, Inc.; Center for Functional Genomics, University at Albany). For obtaining sequences and sequence analysis the following databases and resources were used: NCBI GenBank and Blastp, Welcome Trust Sanger Institute, The Broad Institute and ExPA Sy PROSITE. Accession numbers are Schizosaccharomyces pombe SpPkl1 (Sanger Center, SPAC_3A11.14c); Pkl1 homologs in Schizosaccharomyces cryophilus (Scy) and Schizosaccharomyces octosporus (So, Broad Institute SPOG_02038.3 and SPOG_00465.5, respectively); Homo sapiens HsHSET (KifC1), Mus musculus MmKifC1 and Rattus norvegicus RnKifC1 (NP_002254.2, GB_BAA19676.1, and NP_001005878.1, respectively).

Yeast Strain Constructions.

Integration of the ura4 gene at the cut7 locus was done using a PCR-based gene-targeting approach with long tracts of flanking homology as previously described[66] (Epicentre MasterAmp Extra-Long PCR Kit). We used 500 by homology upstream and downstream of the cut7 open reading frame and verified stable integrants by colony PCR (FIG. 1A). Plasmid Integration was done with pREP vectors using homologous recombination at the autonomous replication site (Mlu1, New England Biolabs). All genetic crosses were done on minimal sporulation media, followed by marker selection and colony PCR.

Synchronous Yeast Culture.

Cultures were grown overnight in YES rich or selective minimal media at 27° C. using baffled flasks. 11 mM hydroxyurea was added to cultures in logarithmic phase and incubated for four hours. Cells were then washed twice with 10 mL sterile water prior to release in fresh media. Depending on the experiment, cells were released at 27° C. (permissive temperature), 32° C. (microtubule repolymerization) or 36° C. (restrictive temperature).

FPLC Sedimentation and Immunoprecipitate Analysis.

Yeast whole cell extracts were prepared using mechanical bead beating (Mini-Beadbeater-16, Biospec) in Buffer P [50 mM Na2PO4 pH 7.2, 10% glycerol, 150 mM NaCl 5 mM ATP, 100 µM GTP] with protease inhibitors (PMSF-1 mM, Luepeptin-50 µM, Pepstatin-2 µM, Aproptinin-175 nM, and Pefabloc-200 µM). Three centrifugations at 17,000×g (1 min, 5 min, 30 min) were used to clarify cell extracts. Separose 6 FPLC was performed as described[15]. For immunoprecipitation, whole cell extracts were incubated with anti-V5-tag mAb-Magnetic beads (MBL International) at 4° C. for 30 minutes. Beads were washed 3× with Buffer P prior to elution by boiling and immediate analysis by Western. Pkl1 peptide co-immunoprecipitation assays were performed as previously described[17]. Antibodies used were primary mouse anti-γ-tubulin monoclonal (1:10,000; Sigma-Aldrich cat. T5326), primary rabbit anti-HA epitope tag (1:5,000; Rockland cat. 600-401-384), primary rabbit anti-FLAG polyclonal (1:320; Sigma-Aldrich cat. F7425), primary mouse anti-V5 monoclonal (1:5,000; Life Technologies cat. R96025) or mouse anti-V5 IgG horseradish peroxidase (HRP)-conjugated monoclonal (1:5,000; Life Technologies cat. R96125), goat anti-rabbit IgG HRP-conjugate (1:20,000; Millipore cat. 12-348) and goat anti-mouse IgG HRP-conjugate (1:10,000; Novagen cat. 71045).

Figure 16:
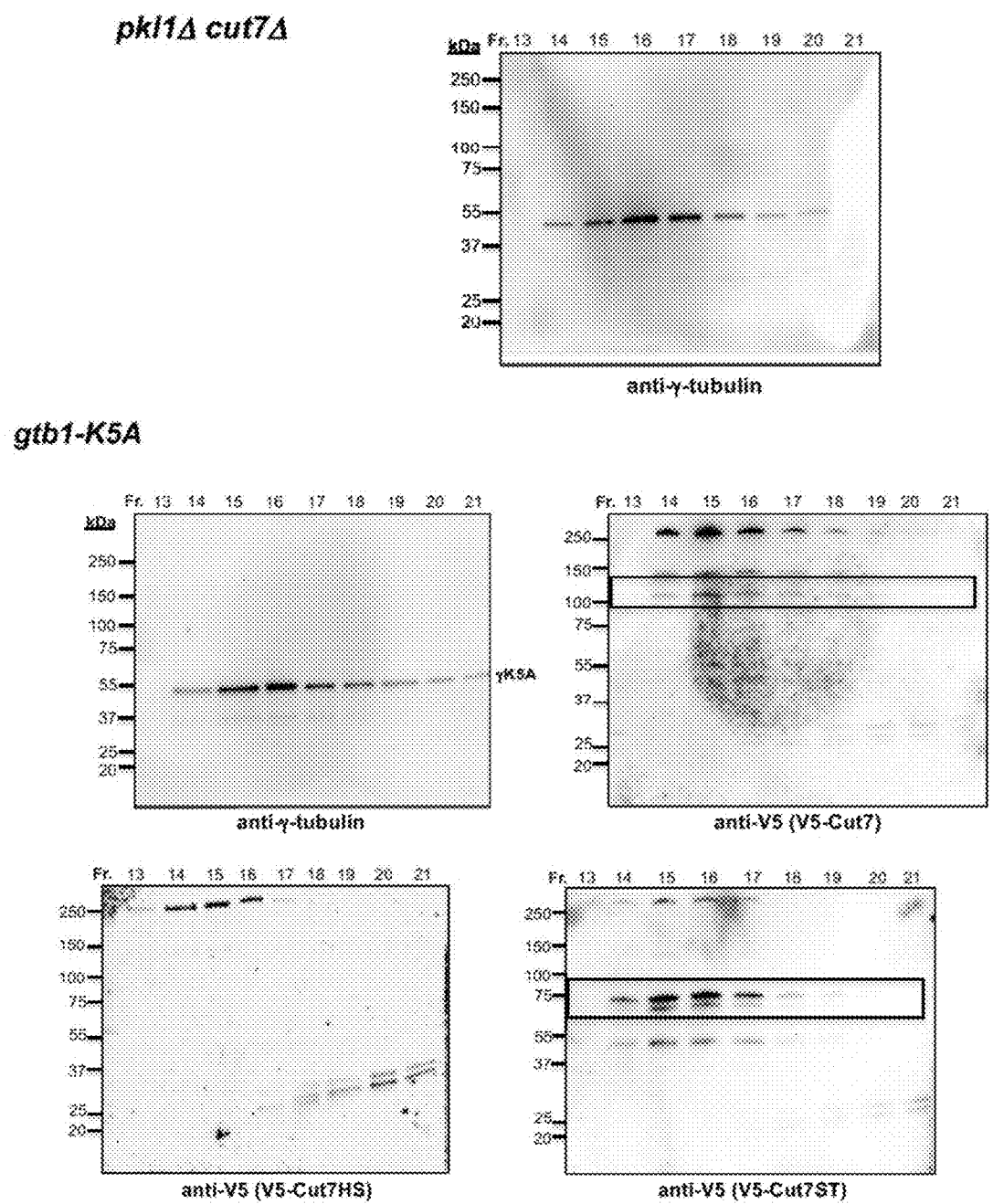
FIG. 16 shows that the Kinesin-5 Cut7 motor domain and BimC domain bind at different sites on the γ-TuRC MTOC. We previously identified that the Pkl1 motor domain binds γ-TuRC by interacting with an external helix (helix 11) on γ-tubulin and identified a mutation in helix 11 (gtb1-K5A) that will block this interaction[22]. By FPLC on Superose 6 as in FIG. 15B, we show that the Cut7 motor domain will not fractionate with the γ-TuRC when the helix 11 (gtb1-K5A mutation is present) and that this mutation does not affect the binding of the BimC domain (Cut7ST) to γ-TuRC.

Human lysates were prepared by harvesting confluent cells with 2 mL TrypLE (Life Technologies) and centrifuging for 5 minutes at 1,000 rpm followed by two washes with 1 mL 1×PBS. Cells were lysed by incubation on ice in RIPA+ Buffer (Tris-HCl pH 7.5, 50 mM, NaCl 150 mM, 1% Triton X-100, 1% Deoxycholic Acid Sodium Salt, 0.1% SDS; supplemented with Luepeptin 5 mM, Pepstatin 2 µM, Aprotinin 175 nM, PMSF 1 mM+GTP 100 µM) for 45 minutes, mixing occasionally. Lysates were clarified by centrifugation at 14,000 RPM (20,817×g) at 4° C. for 1 hour. Peptide co-immunoprecipitation assays were performed as above. Antibodies used for Western blots were primary mouse anti-γ-tubulin monoclonal (1:9,000; Sigma-Aldrich cat. T5326) and primary rabbit anti-GCP2 polyclonal (1:2, 000; Thermo Scientific cat. PIPA521433). The secondary antibodies mentioned above were used for detection by HRP. Uncropped scans of Western blots are provided in FIG. 15 and FIG. 16.

Breast Cancer Cell Culture and Peptide Transfection.

MCF-7 and MDA-MB-231 (ATCC) cells were maintained in 25 cm² tissue culture treated Corning flasks (Sigma-Aldrich) in DMEM complete medium with Glutamax-1 and supplemented with 10% fetal bovine serum. MCF-7 DMEM complete medium was additionally supplemented with 0.01 mg/mL bovine insulin (Sigma-Aldrich). Flasks were maintained at 37° C. in 5% $CO_2$, 95% air, and cells were passaged every 5-7 days using 1 mL TrypLE (Life Technologies).

For live cell peptide transfection we used the Chariot system (Active Motif) according to the manufacturer's instructions. Cells were seeded into 35 mm tissue culture-treated dishes containing coverslips and grown in complete medium to ~60% confluency. 1 µg of Kinesin-14 Tail peptide PγTR (GenScript) was diluted in 100 µL 1×PBS on ice. 6 µL of 1/10 PBS-diluted Chariot reagent was further diluted into 100 µL sterile water on ice in a separate tube. Diluted peptide and diluted Chariot were combined and incubated at room temperature for 30 minutes to allow the Chariot-peptide complex to form. Following incubation, media was aspirated from cells, which were then washed once in 1×PBS. The entire 200 µL volume was added to cells in 400 µL serum-free media and gently rocked to ensure even delivery. Plates were returned to 37° C. for 1 hr. Next, DMEM complete growth medium was added to 2 mL without removing the peptide delivery solution (108 µM peptide in 2 mL). Cells were further incubated at 37° C. overnight and fixed after 24 hours.

Fluorescence Microscopy and Immunocytochemistry.

Figure 8A:
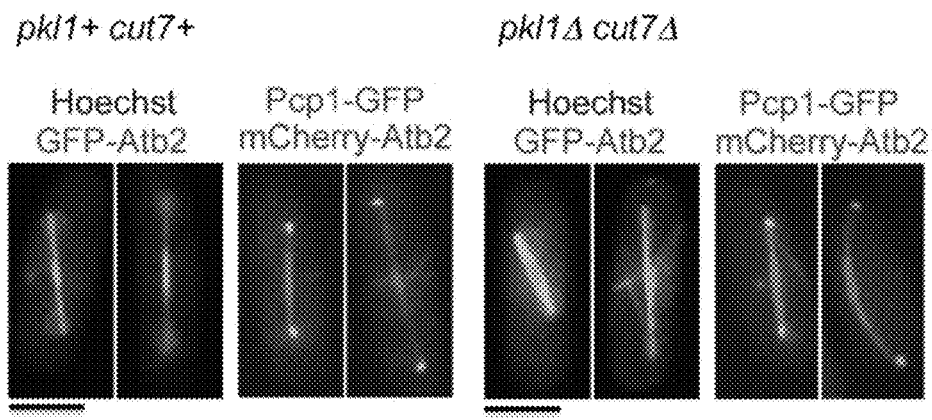
FIGS. 8A-E show that spindle width is increased in pkl1Δ and pkl1Δ cut7Δ cells. (A) Live cell fluorescence imaging reveals differences in spindle thickness between wild type (pkl1+ cut7+) and pkl1Δ cut7Δ double mutant cells. Two stages of mitosis are shown with different markers. On the left, GFP-Atb2 marks microtubules (α-tubulin, green) and DNA is stained with Hoechst (blue). On the right, microtubules are marked by mCherry-Atb2 (red) and spindle pole bodies are marked by Pcp1-GFP (green). (B) Differences in spindles thickness in a wild type/pkl1Δ cut7Δ mixed culture by live cell fluorescence microscopy. (C) Frequency of thick spindles in wild type, pkl1Δ and pkl1Δ cut7Δ cells (mean±s.e.m., n=90 cells for each, *P<0.05 by Student's t test). (D) Live cell fluorescence microscopy of wild type and pkl1Δ cut7Δ cells with mCherry-Atb2 and Klp9-GFP suggests that the increased spindle thickness we observe is due to parallel microtubules that emanate from a single pole (highlighted by cartoon schematics). Klp9-GFP marks antiparallel microtubules at the spindle midzone. In the schematic, yellow marks Klp9-GFP/antiparallel microtubule overlap, red marks parallel microtubules that extend from either pole (white circle), and green is Klp9-GFP signal on chromatin. Images were oriented similarly for convenience. Similar results to pkl1Δ cut7Δ cells were observed for the pkl1Δ single mutant. (E) Plating of wild type, pkl1Δ and pkl1Δ cut7Δ (top to bottom) cells on medium containing three concentrations of the microtubule-depolymerizing drug TBZ (0 μg/mL left, 10 μg/mL middle, 20 μg/mL right). All scale bars in this figure are 5 μm.
Figure 8B:
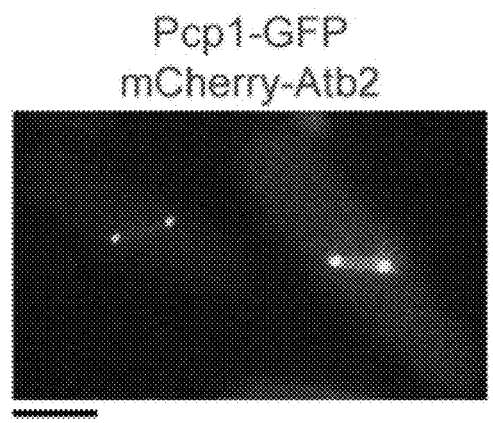
Figure 8C:
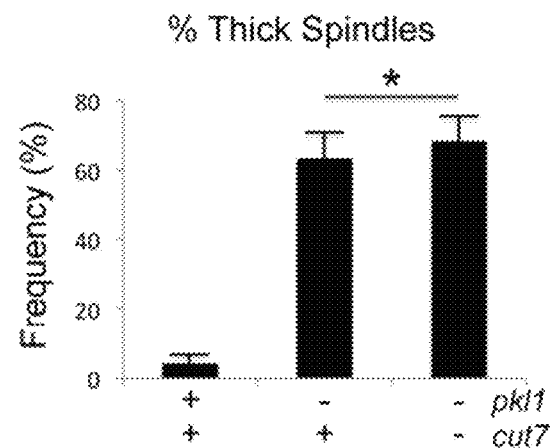

Fluorescence microscopy was performed using Zeiss Observer.Z1 inverted microscope with 63× Plan-Apochromat 1.4 NA oil and 100× oil 1.45 PIanFLUAR DIC objectives. Data was obtained using a Hamamatsu ORCA ER CCD camera with Zeiss Axiovision Rel 4.8 acquisition software. We acquired 20-image 0.1 µm Z-stacks. Timelapse series were acquired every 30 seconds to 6 minutes, with a median interval of 2 minutes. 10-image 0.1-micron Z-stacks were superimposed on each timelapse image in a series. With live cells, GFP-Atb2 was imaged at 50-60 ms exposure and mCherry-Atb2 was imaged at 500 ms exposure. Only GFP-Atb2 was used in timelapse. Average temperature in the imaging room was 23° C. Using −20° C. methanol fixation we were able to preserve GFP signal for quantifying phenotypes. In immunocytochemistry, microtubules were stained with primary TAT1 antibody (1:25)[67], followed by secondary goat anti-mouse Alexa Fluor 488 IgG (1:50; Life Technologies cat. A-11001) and DNA was stained in 1 µg/mL Hoechst. Monoclonal anti-V5 primary antibody conjugated to FITC was used for viewing V5-tagged Cut7 constructs in fixed cells (1:500; Life Technologies cat. R963-25). Cells were imaged immediately using the Zeiss Observer.ZI system. In FIG. 8e, zoomed images were made high contrast. Z-stacks were made into 2D projections using ImageJ. Cold depolymerization and repolymerization of in vivo microtubules was performed as previously described[68]. Wild type and pkl1Δ cut7Δ cells containing the integrated GFP-atb2 (α-tubulin) plasmid were fixed to preserve GFP signal and analyzed using the Zeiss system.

Human cells were fixed on glass coverslips in −20° C. methanol for 10 minutes, washed with 1×PBS and permeabilized in 0.5% Triton X-100 for 20 minutes. Following further washes, cells were blocked for 30 minutes in 1% bovine serum albumin/knock out serum replacement (BSA/KOSR). For peptide localization to centrosomes, 1 μg/mL of peptide was applied after blocking and before primary antibody application. Antibodies used were primary mouse anti-γ-tubulin monoclonal (1:5,000; Sigma-Aldrich cat. T5326) or primary mouse anti-α-tubulin monoclonal DM1A (1:1,000; Santa Cruz Biotech cat. sc-32293), primary His-tag polyclonal antibody (1:1,000; Cell Signaling cat. 2365), secondary goat anti-mouse Alexa Fluor 488 IgG (1:1,000; Life Technologies cat. A-11001) and secondary goat anti-rabbit Texas Red (1:1,000; Life Technologies cat. T-6391). Antibodies were diluted in 1% BSA/KOSR antibody dilution buffer. After secondary antibody application and washes, DNA was stained with 1 μg/mL Hoechst solution in 1×PBS for 10 minutes followed by 3× final PBS washes and mounted on slides with ProLong Gold anti-fade (Life Technologies). 40-image 0.1 μm Z-stacks were made into maximum intensity 2D projections using ImageJ.

In Vitro Microtubule Nucleation Assays.

In vitro microtubule nucleation assays were performed in a total volume of 5 μL. That is, 3 μL for the sample and 2 μL of tubulin at a 1:5 ratio of Rhodamine:unlabeled tubulin (Cytoskeleton, Inc.). Total tubulin concentration was 3.75 μg/μL in 2.5× tubulin working buffer (2.5×BRB80: 200 mM PIPES, 2.5 mM $MgCl_2$, 2.5 mM EGTA at pH 6.8 and 2.5 mM GTP). For whole cell extract nucleation analysis with peptide, 2 μL of whole cell extract was added with 1 μL of peptide at 300 nM for a final peptide concentration of 60 nM. This 3 μL combination was added first followed by tubulin working buffer. For samples with no peptide, the 5 μL final volume was comprised of 3 μL RIPA buffer and 2 μL of whole cell extract. The 5 μL reaction was combined on ice, quickly spun and returned to ice before incubating in a 37° C. water bath for 4 minutes. Sample incubation was staggered at 20 s intervals to allow for pipetting. After 4 minutes, 50 μL of 1% glutaraldehyde fixing solution was added and tubes were incubated at room temperature for 3 minutes. Samples were completed by addition of 1 mL 1×BRB80, inverting multiple times to mix. For analysis, 50 μl of this mixture per sample was sedimented by ultracentrifugation at 173,000×g through a 15% glycerol cushion onto glass cover slips and imaged by Rhodamine epifluorescence using the Zeiss system at 630×. Images of multiple fields were collected and the average microtubule number per field was determined.

Structural Analysis.

PyMol molecular visualization software (V1.5) was used for structural analysis of the conserved α-β-tubulin heterodimer 1TUB[10] and conserved γ-tubulin monomer 1Z5V[6,11,14,69] in FIG. 3.

Statistical Analysis.

For statistical analysis of phenotypes, n values were chosen as number of cells per strain needed to ensure adequate power to detect significant outcomes. P-values were generated using Student's t-test and statistical significance was considered for $P<0.05$ as appropriate. All statistical data in this study is reported as mean±s.d. or ±s.e.m.,
as indicated. For cell cycle arrest by 1 μg transfection of PγTR, 12 fields at 200× were counted. Arrested cells with positive peptide signal were taken as a percentage of the entire population. Cells that were negative for peptide signal did not arrest.

Kinesin-5 is Dispensable in the Absence of Kinesin-14 Pkl1.

Figure 1B:
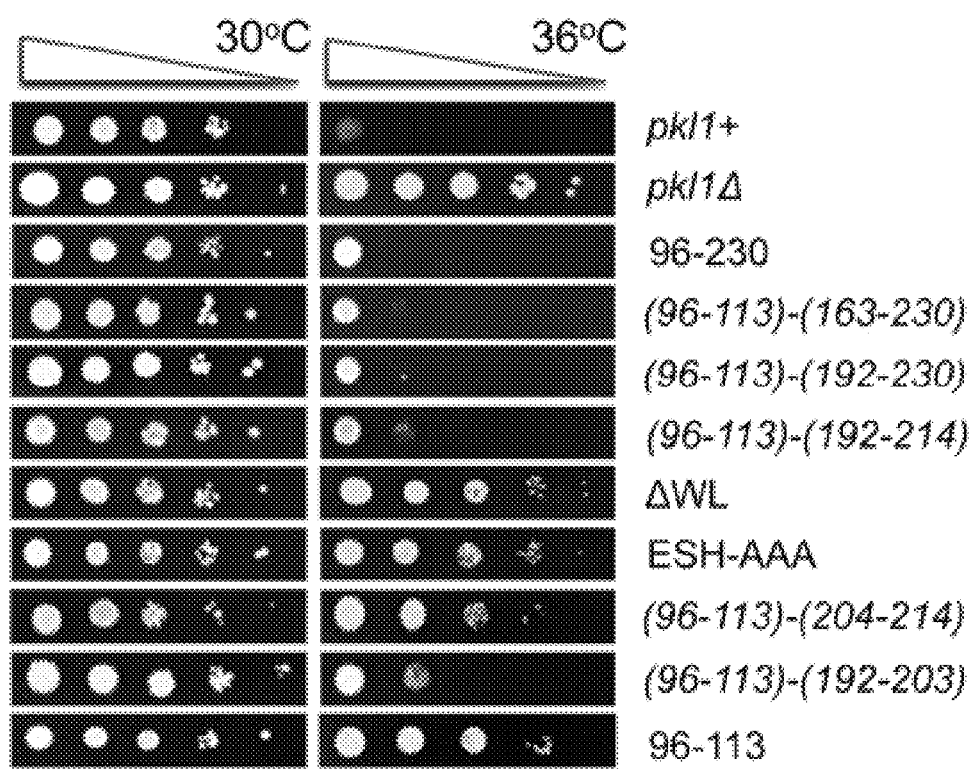
Figure 1C:
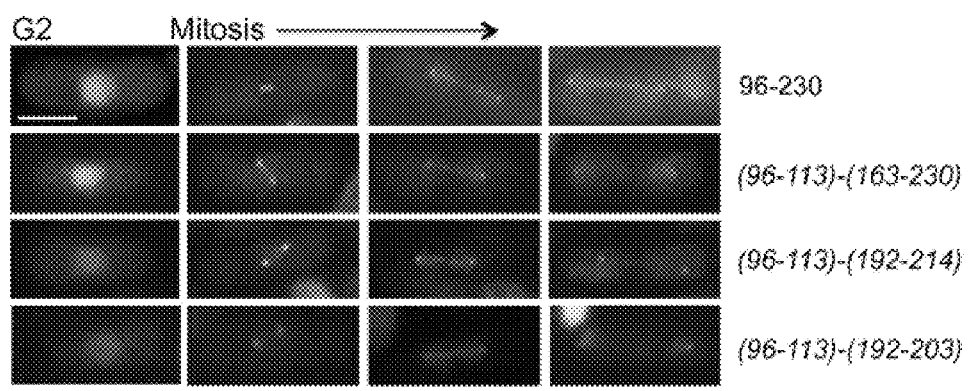
Figure 1D:
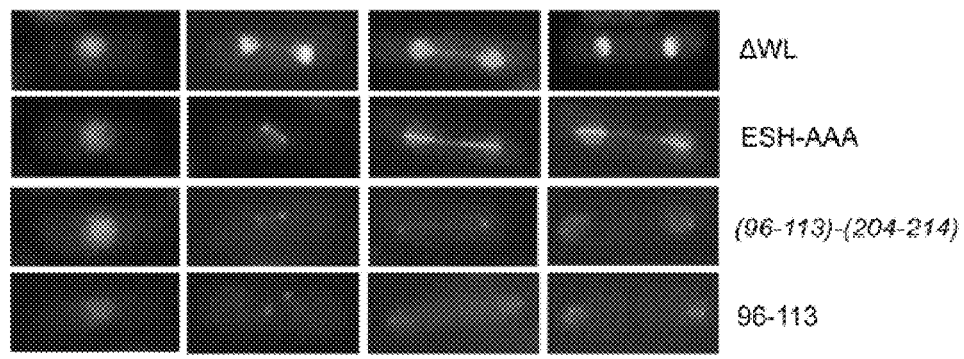

Spindle bipolarity in fission yeast requires Kinesin-5 Cut7[27]. The mechanism underlying its essential nature remains unclear as another Klp, Kinesin-6 Klp9, is capable of crosslinking antiparallel microtubules and is required for spindle elongation[28]. In eukaryotes, an opposing relationship between Kinesin-5 and Kinesin-14 Klps in microtubule regulation is highly conserved. We previously demonstrated that Kinesin-14 Pkl1 directly binds and down regulates γ-TuRC function[17,23]. We tested the hypothesis that a required role of Kinesin-5 Cut7 (cut7 gene), which localizes at spindle poles, is to oppose Kinesin-14 Pkl1 (pkl1 gene). By homologous recombination (FIG. 1A) we simultaneously deleted the cut7 gene whilst marking the locus with ura4 (cut7,6::ura4+) in a strain deleted for Pkl1 (pkl1Δ::his3+). The pkl1Δ cut7Δ double mutant strain exhibits robust viability by serial growth assays, similar to wild type cells (FIG. 1B). Spindle pole body (SPB) separation is not affected in the double mutant pkl1Δ cut7Δ versus wild type (FIG. 1C,D) nor is mitotic progression through anaphase affected as compared to wild type or pkl1Δ strains (FIG. 1C,E-G). However spindle breakdown is delayed as indicated by a persistent spindle following anaphase B elongation (FIG. 1C,G). We demonstrate that Kinesin-5 Cut7 is dispensable in the absence of Pkl1, indicating that a Kinesin-5 independent mechanism for spindle assembly can exist in fission yeast. This also supports a required role for Cut7 that is to counter Pkl1, which is a direct negative regulator of the γ-TuRC MTOC.

Kinesin-5 Cut7 Binds γ-TuRC Through Motor and Tail Domains.

Kinesin-14 Pkl1 negatively regulates γ-TuRC through two internal protein domains that include elements of its Motor and Tail regions[17,22]. To determine if Cut7 binds the γ-TuRC MTOC by a similar mechanism Fast Protein Liquid Chromatography (FPLC)[15,17] using V5-tagged deletion derivatives of Cut7 previously generated[29], immunocytology using newly generated V5-tagged deletion and site-directed mutagenesis derivatives and Pkl1 peptide co-immunoprecipitation assays (FIG. 2) were used. Fractionation of whole cell extracts carrying V5-tagged full length Cut7 and two Cut7 truncation constructs (Cut7-Head-Stalk or Cut7HS, aa 1-88; Cut7-Stalk-Tail or Cut7-ST, aa 443-1,085) were examined in the pkl1Δ cut7Δ double mutant and in the gtb1-K5A strain that inhibits Pkl1 regulation of γ-TuRC by blocking its Motor domain binding to γ-tubulin (FIG. 2A,B, FIG. 3A-C)[22]. A FLAG-tagged truncated Pkl1 construct that retains full function and localizes to γ-TuRC (pkl1Δ95)[23] was used as a positive control along with Alp4 (gamma complex protein GCP2 yeast ortholog) and γ-tubulin proteins that are core subunits of the γ-TuSC and the >2,000 kDa high molecular weight γ-TuRC MTOC. The γ-TuRC peaks in FPLC fractions 15 and 16 (FIG. 2B). Profiles of the three cut7 constructs in pkl1Δ cut7Δ double mutant cells that are pREP81V5/cut7, pREP81V5/cut7HS and pREP81V5/cut7ST are shown (FIG. 2A,B). Western blot analysis following FPLC fractionation reveals that Cut7, Cut7HS and Cut7ST exhibit similar high molecular weight profiles as Pkl1Δ95 and all peak in identical fractions to core γ-TuRC proteins γ-tubulin and Alp4. To further confirm Cut7ST binding to γ-TuRC we performed co-immunoprecipitations from high molecular weight FPLC fraction 15 in strain alp4-HA pREP81V5/cut7ST (FIG. 2D,E). Magnetic beads with histidine affinity were conjugated to small His-tagged Pkl1 Tail peptides (PγT or PγM)[17] that bind γ-TuRC (PγT, targeting) or cannot interact with fission yeast γ-TuRC (PγM, mutated). Using this approach, we detect γ-TuRC core subunit proteins γ-tubulin and Alp4-HA in addition to Cut7ST (V5 tag) by Western blot analysis after elution off of beads (PγT). These proteins were not recovered by the mutated peptide, as expected. We were unable to detect α-/β-tubulin in high molecular weight fractions following FPLC, which further suggests that the Klps detected were directly bound to γ-TuRC.

Figure 3A:
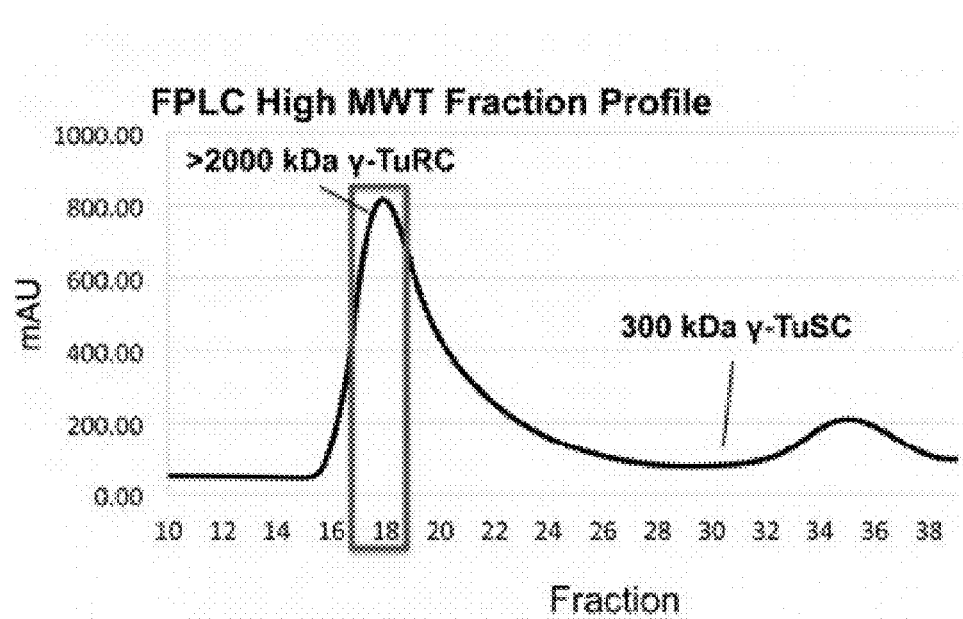
FIGS. 3A-C show that novel kinesin-14 Tail elements for γ-TuRC binding and γ-tubulin release. Peptide assays. (A) Profile of γ-TuRC isolation on Superose 6. MWTs of γ-TuRC and γ-TuSC are indicated along with two MWT markers (2000 kDa Blue Dextran, 443 kDa Apoferritin). High MWT fraction 17, indicated in red, was used in subsequent assays. (B) Co-immunoprecipitation (Co-IP) of γ-TuRC occurs with P1, as indicated by westerns of γ-TuSC subunit components Alp4, Alp6 and γ-tubulin. P2 is unable to interact with γ-TuRC as expected. P3 binds to γ-tubulin. Silver stains of the His bead elution indicates γ-TuRC is initially bound but comes off in pre-elution washes shown in (C).
Figure 3B:
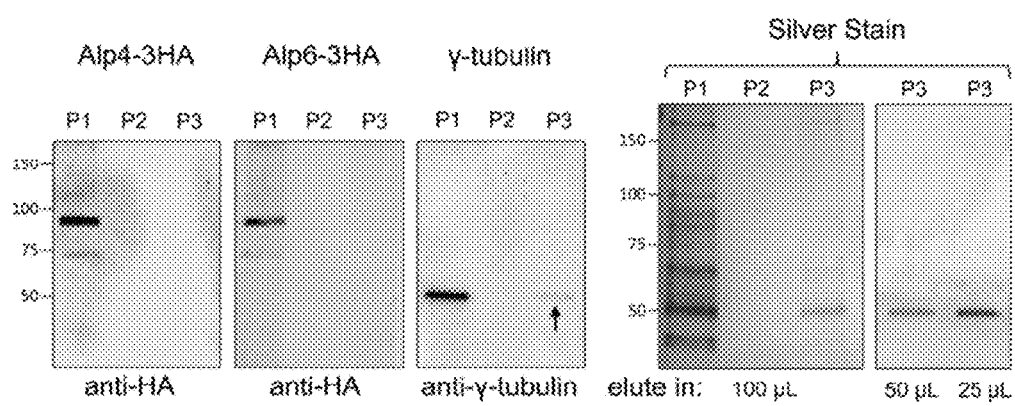
Figure 3C:
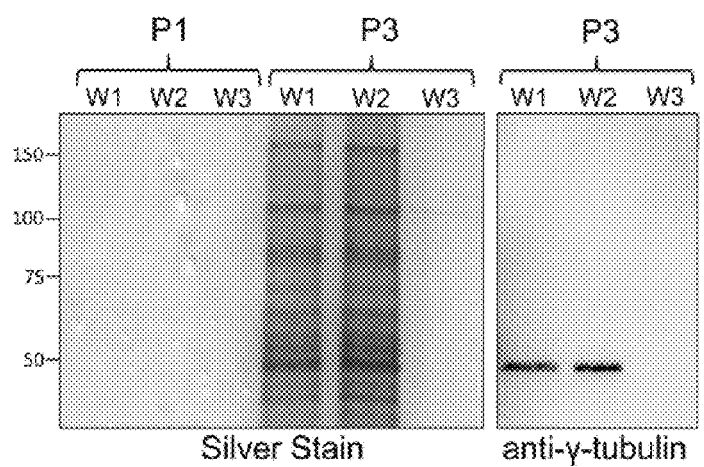

We previously demonstrated that mutation of a conserved lysine residue to alanine in γ-tubulin helix 11 (gtb1-K5A) abolishes Pkl1 Motor domain binding to γ-TuRC and blocks its full function in vivo[22]. To determine if Cut7 similarly binds to γ-tubulin through helix 11 we examined its FPLC profile in the gtb1-K5A strain (FIG. 3A). The mutant γ-tubulin-K5A fractionates similarly to wild type γ-tubulin by FPLC. The V5-Cut7 signal in high molecular weight γ-TuRC fractions is significantly reduced in the gtb1-K5A strain, whereas steady-state expression levels of V5-Cut7 in gtb1 wild type and gtb1-K5A mutant backgrounds by Western blot analysis of whole cell extracts is similar (FIG. 3C). Fluorescence microscopy of V5-Cut7 in the gtb1-K5A mutant reveals that while pole localization is reduced, Cut7 retains localization to spindle microtubules, which is enhanced. Truncated Cut7HS that contains the Cut7 Motor and Stalk domains and lacks the Tail is completely absent from high molecular weight γ-TuRC fractions in the gtb1-K5A background (FIG. 3A). Similarly to V5-Cut7 it retains the ability to bind to spindle microtubules as observed by immunocytology (FIG. 3D). Interestingly, the truncated Cut7ST protein in this strain that does not retain the Motor domain is unaltered in its association with γ-TuRC (FIG. 3A). The V5-Cut7ST with a fused nuclear localization single (NLS) to allow nuclear localization[29] is sufficient to target spindle poles in mitosis (FIG. 3D). This indicates that, similar to Pkl1, Cut7 contains distinct Motor and Tail domain elements that offer independent binding sites to γ-TuRC.

The Kinesin-5 Cut7 BimC Tail Element Directs Pole Targeting.

The eukaryotic BimC domain is highly conserved across Kinesin-5 members[30,31]. The domain was first identified in the *Aspergillus nidulans* Kinesin-5 BimC protein[32], but its precise role in mitosis has remained unknown for two decades. To examine the consequences of a mutation to the BimC domain of Cut7 on spindle pole localization we used the loss of function temperature sensitive allele cut7-22 that contains a single point mutation within this region (1,021 Pro to Ser)[22]. To determine if the BimC box is the primary spindle pole targeting site in the Cut7 Tail domain, we utilized V5-tagged Cut7 deletion and/or site-directed mutagenesis constructs with a fused NLS (FIG. 3E)[23]. These constructs encode the fusion proteins V5-NLS-Cut7ST, V5-NLS-Cut7ST[22] (point mutation at 1,021 Pro to Ser resulting in lost bipolarity)[22], V5-NLS-Cut7T (Cut7-Tail, aa 888-1,085) and V5-NLS-Cut7T[22] and were analyzed by immunocytochemistry of pkl1Δ cut7Δ cells that were fixed after shifting to 36° C. V5-NLS-Cut7ST and V5-NLS-Cut7T lack the Motor domain and retain spindle pole localization. In contrast, mutated V5-NLS-Cut7ST[22] and V5-NLS-Cut7T[22] constructs are unable to localize to poles but are expressed and retained within the nucleus, suggesting that the BimC sequence constitutes a key domain in the Cut7/γ-TuRC interaction. Together, our data support the model in which Cut7 interacts physically with the γ-TuRC MTOC in a manner poised to allow opposition to Pkl1 activity.

Pkl1 Regulates Spindle Morphology from γ-TuRC.

Figure 4A:
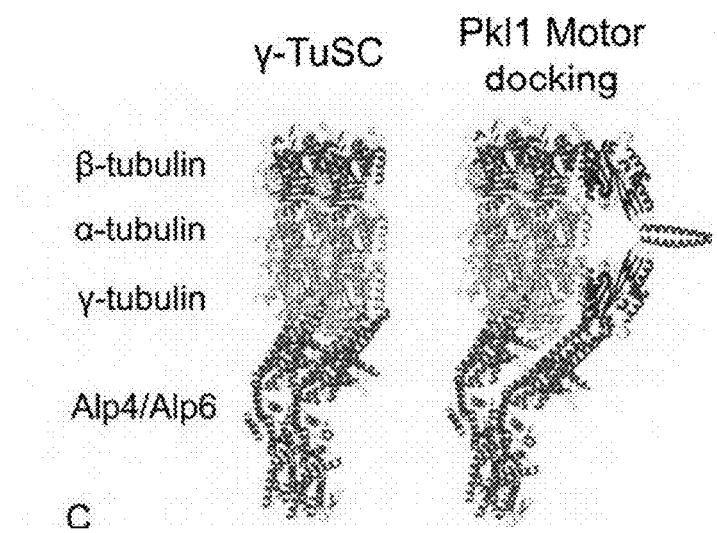
FIGS. 4A-D show a model for the mechanism of *S. ponbe* kinesin-14 Pkl1 regulation of γ-TuRC. Pkl1 associates with the γ-TuRC in vivo to regulate bipolar spindle assembly through Tail and Motor domain interactions. The Pkl1 Motor domain (A) binds to γ-tubulin at helix 11, directly adjacent to proposed binding sites of γ-TuSC proteins to γ-tubulin (Alp4 and Alp6 in fission yeast). These adjacent sites may partially overlap. If so, Pkl1 binding could destabilize Alp4/Alp6 interactions with γ-tubulin, priming the system for severing by the Tail domain. This is consistent with enhanced kinesin-14 activity in the presence of the Motor domain in vivo. These concepts are illustrated in (B). We propose that two elements of the Pkl1 Tail contribute to this mechanism in different ways, providing γ-TuRC binding and γ-tublin severing activities. The expected outcome of Motor and Tail activities is to remove γ-tubulin from γ-TuSC and result in conformational inactivation of Alp4/Alp6 as shown in (C). The consequence of these actions on microtubules is expected to result in capped microtubule minus ends (D). However, full removal of γ-tubulin from microtubule minus ends as well as γ-TuRC may alternatively result in partial or full microtubule depolymerization. The ability of the γ-TuRC to recover from kinesin-14 action is unclear.
Figure 4B:
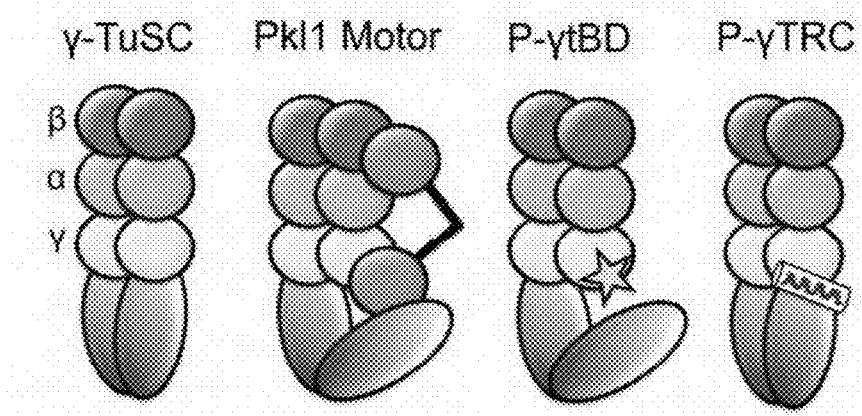
Figure 4C:
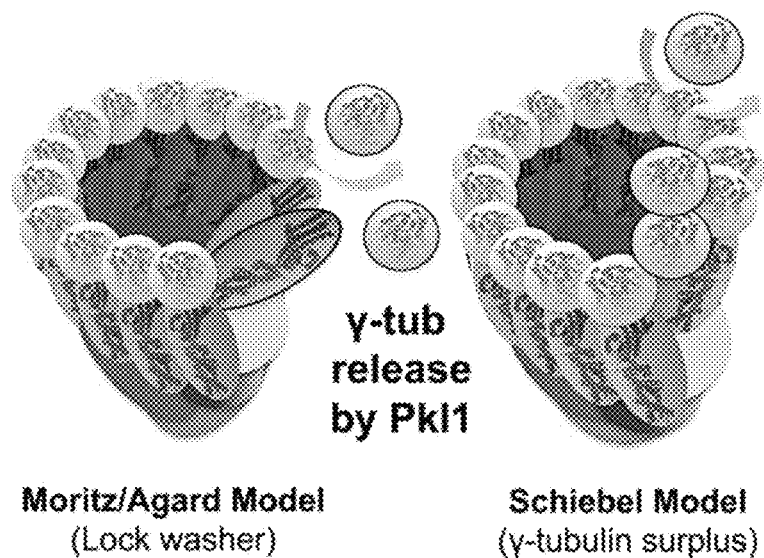

Mitotic phenotypes in strains carrying single pkl1Δ or pkl1Δ cut7Δ double mutants versus wild type were evaluated by live cell and timelapse imaging of microtubules (α-tubulin as mCherry-Atb2 or GFP-Atb2), spindle poles (γ-TuRC pericentrin protein 1, Pcp1-GFP), antiparallel microtubules and chromatin (anaphase B and chromatin binding Kinesin-6 member Klp9-GFP) as well as Hoechst staining of DNA. An increase in spindle thickness is observed in the pkl1Δ cut7Δ double mutant strain versus wild type as seen in single strain imaging (FIG. 4a) or by live cell imaging of a mixed culture with wild type cells (FIG. 4b). This increased thickness is also present in the pkl1Δ strain (FIG. 4c). In FIG. 4b, the ratio of double mutant to wild type cells at 2:1 resulted in an accordant increase in the ratio of thick:thin spindles. Thick spindles (>0.5 μm in a spindle of length 4 to 6 μm) are observed in 4±2% of wild type cells, 63±8% pkl1Δ single mutant and 68±8% of pkl1Δ cut7Δ double mutant cells (mean±s.e.m., n=90 cells for each strain). Although the pkl1Δ cut7Δ double mutant background generates a slight increase in the thick spindle phenotype (P<0.05 by Student's t-test), the change versus pkl1Δ single mutant alone is small. This indicates that it is primarily the loss of Pkl1 that induces this phenotype, which is exacerbated by additional loss of Cut7.

Figure 4D:
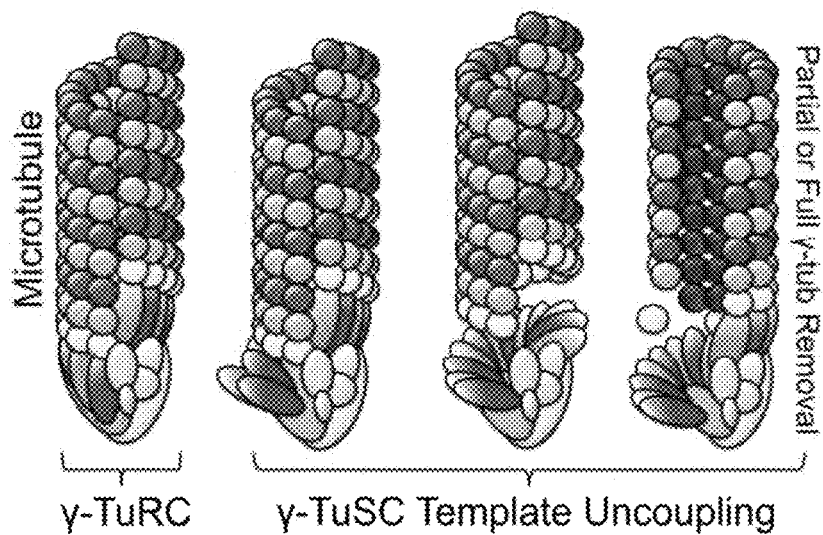
Figure 5A:
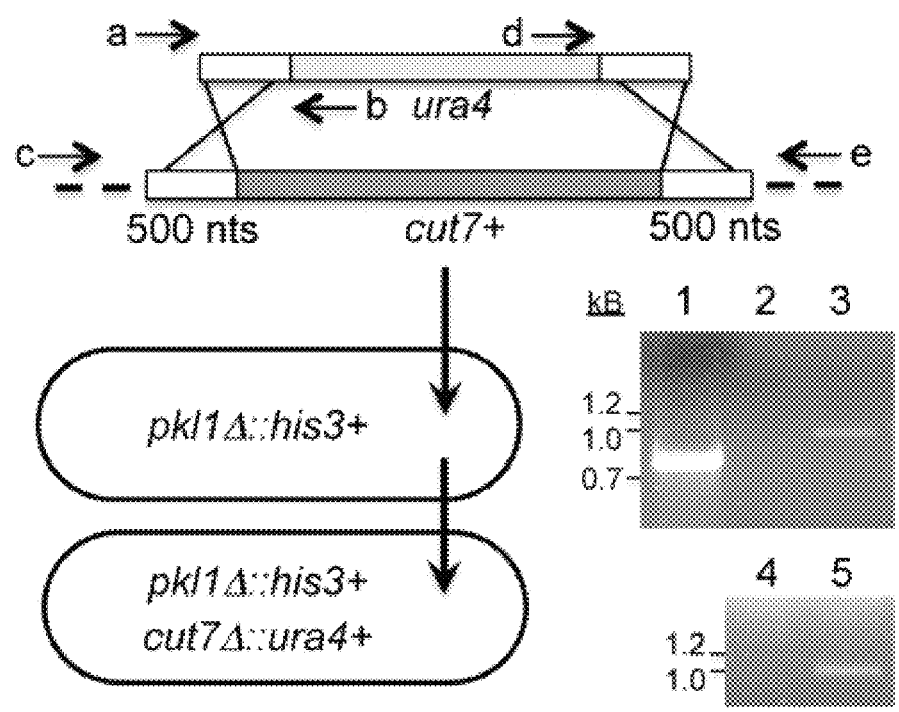
FIGS. 5A-G show that spindle assembly and cell viability remain high in the pkl1Δ cut7Δ strain. (A) cut7 knockout and integration of ura4+ at this locus in the pkl1Δ::his3+ single mutant. The PCR-based approach used long (500 nts) flanking tracts of homology and the genomic deletion/integration event was confirmed by colony PCR (lane 3: 5', lane 5: 3' oligonucleotide pairs b and c, d and e, respectively). Lane 1 is a positive control using oligonucleotide pair a and b. Lanes 2 and 4 are negative controls using oligonucleotide pair b and c on pkl1Δ single mutant cells. (B) Serial dilution growth assays at 25° C. permissive and 36° C. restrictive temperatures (top). Cells were plated on rich YES plates at increasing dilution. Cell viability was analyzed by Phloxine B stain (bottom). (C) Average spindle pole body separation versus time (Pcp1-GFP) for wild type (green curve; n=5 time series), pkl1Δ single mutant (red curve; n=7 time series) and pkl1Δ cut7Δ double mutant cells (purple curve; n=9 time series) following hydroxyurea synchronization. (D) Timelapse fluorescence microscopy of prophase spindle pole body separation in wild type and pkl1Δ cut7Δ cells using spindle pole marker Pcp1-GFP. Timelapse fluorescence microscopy of mitosis from metaphase is shown for wild type in (E), pkl1Δ in (F) and pkl1Δ cut7Δ in (G). GFP-Atb2 marks microtubules (green) and DNA is stained with Hoechst (blue). All scale bars in this figure are 5 μm.
Figure 5B:
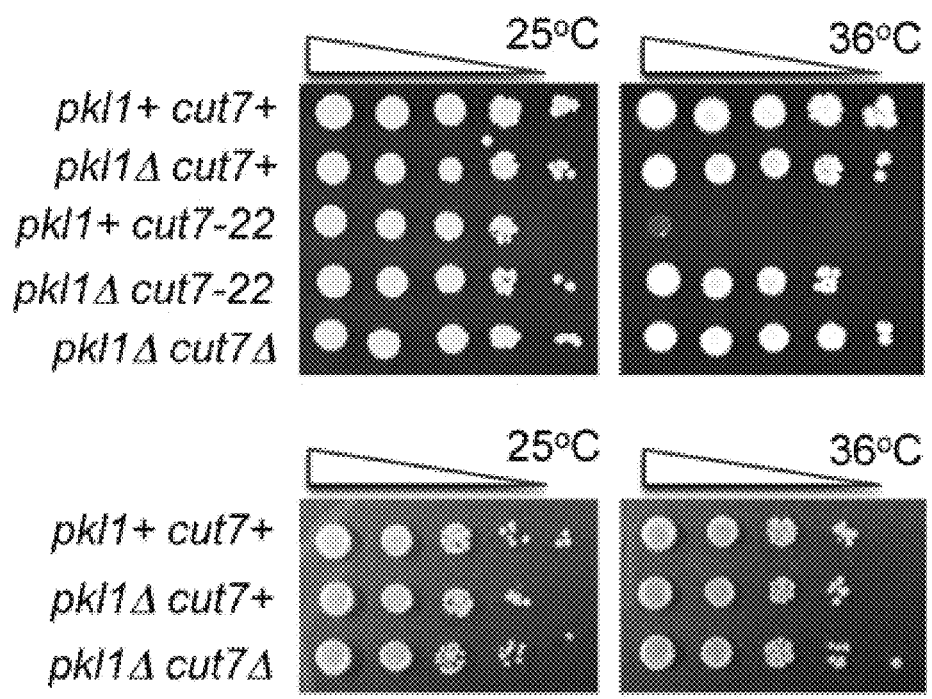
Figure 5C:
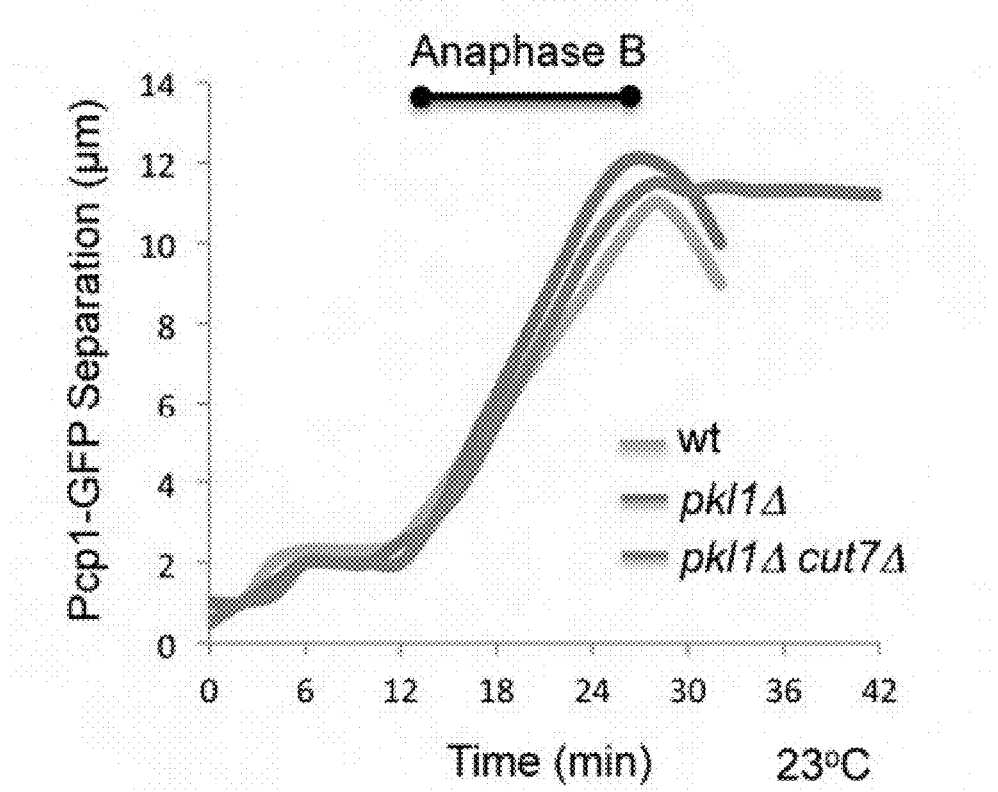
Figure 5D:
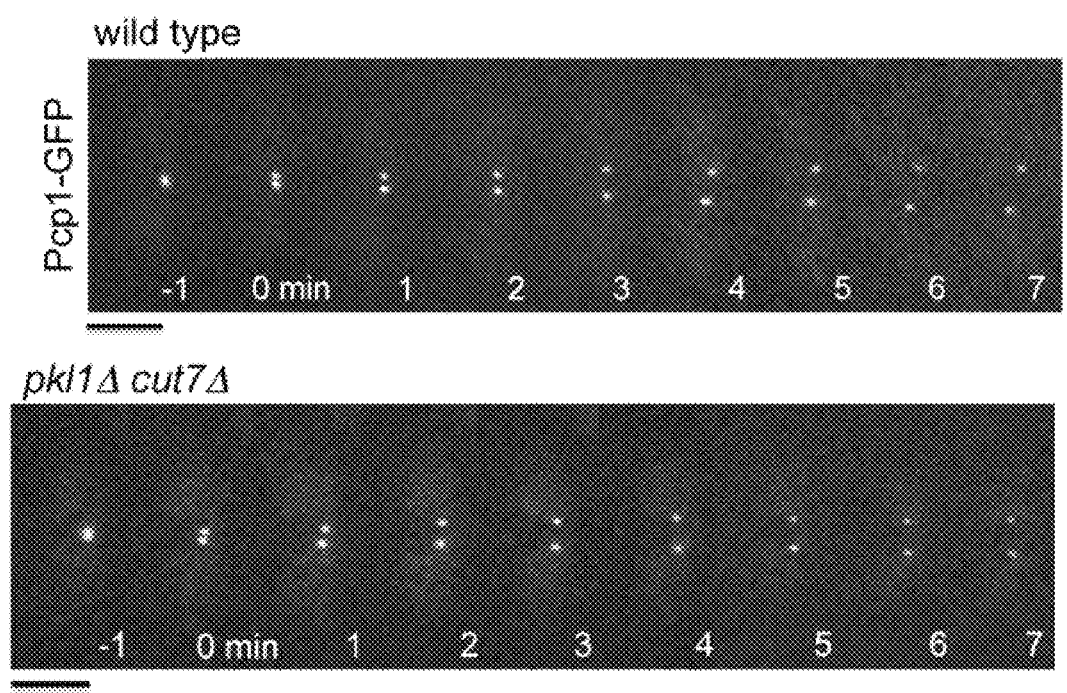
Figure 5E:
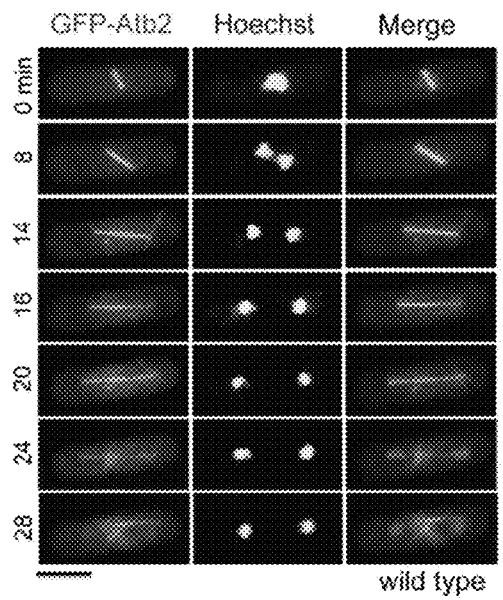
Figure 5F:
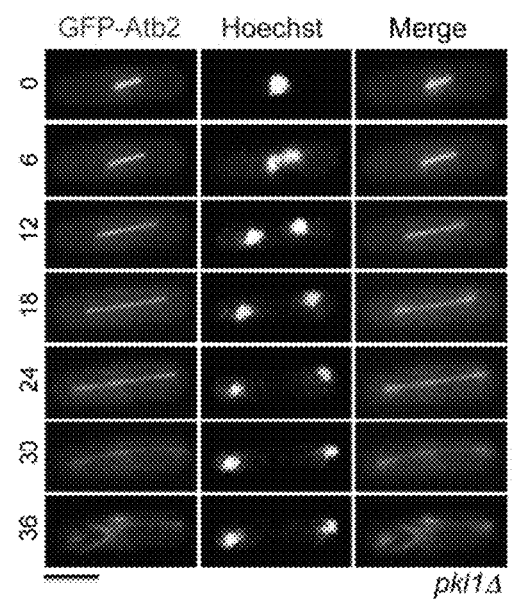
Figure 5G:
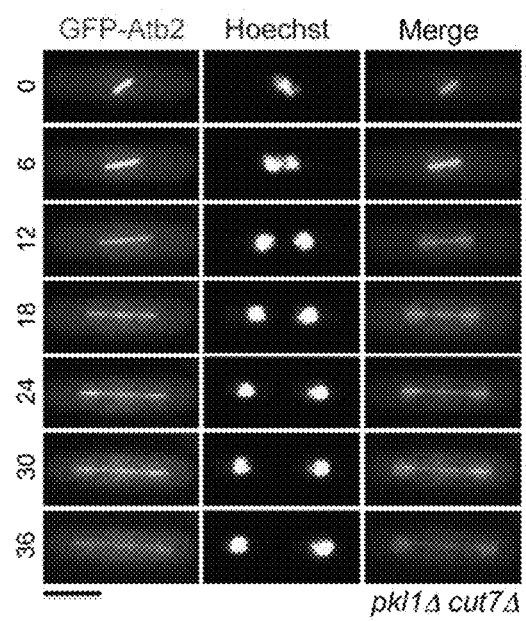

The nature of the morphological change to spindle thickness could be the result of an increase in the number of antiparallel microtubules from both poles, parallel microtubules that emanate from a single pole, or due to unattached microtubules or disorganized arrays[20] at a single pole. To distinguish amongst these possibilities we used multiple approaches. Kinesin-6 Klp9-GFP crosslinks antiparallel microtubule arrays[28] and can be used to preferentially mark the extent of microtubule overlap (generally midzone) and is used with α-tubulin (mCherry-Atb2) to visualize spindle microtubules and length of the mitotic spindle. In wild type cells, the Klp9-GFP signal spans the entire spindle midzone width (FIG. 4D, left images), whereas in the double mutant (FIG. 4D, right images) we observe microtubule staining adjacent to the zone of antiparallel overlap that appears to emanate primarily from a single pole. We do not detect increased resistance to the microtubule-depolymerizing drug Thiabendazole (TBZ) in pkl1Δ or pkl1Δ cut7Δ strains versus wild type (FIG. 4E) consistent with no or limited changes to microtubule number. We favor the interpretation that increased spindle width is likely due to asymmetric spindle pole effects (lost organization) in the absence of Pkl1 as seen in ref. 20 and not to an increased number of spindle microtubules.

Morphological changes in spindle thickness do not affect mitotic progression in the pkl1Δ cut7Δ double mutant cells through anaphase as seen by timelapse imaging and kymographic analysis versus wild type (FIG. 5). However, following anaphase B, timely spindle breakdown is delayed in a significant percentage of pkl1Δ cut7Δ cells. In 78% of double mutant cells (n=15 timelapse series) spindles remain intact significantly longer than wild type (n=7 timelapse series) for an additional 24±7 min, and can persist beyond formation of equatorial MTOC arrays (FIG. 5A-C). Three patterns of spindle microtubule density in pkl1Δ cut7Δ anaphase cells were observed (FIG. 5A-C,E) and are referred to as Type 1, Type 2 and Type 3. In Type 1, central microtubule antiparallel overlap is identical to wild type. In Type 2, microtubule density is highly biased to one pole and in Type 3, central microtubules are diminished compared to thicker pole-biased microtubules. The relative frequencies of these patterns averaged over three time points after hydroxyurea synchronization (120, 140 and 160 min) are indicated in a stacked histogram (FIG. 5F). Our findings indicate that changes occur to spindle width and organization in both the pkl1Δ cut7Δ double mutant and pkl1Δ single mutant strains. Thickness along the spindle length is distributed in three patterns, two that are distinct from wild type. Spindle morphology phenotypes in the pkl1Δ cut7Δ double mutant are only modestly altered versus the single pkl1Δ mutant strain. These findings indicate that Kinesin-14 Pkl1 is the primary kinesin regulating microtubule organization at γ-TuRC, a loss that results in broader spindles with asymmetric microtubule density along the spindle length.

Daughter Pole Disorganization Persists in the Double Mutant.

Figure 6A:
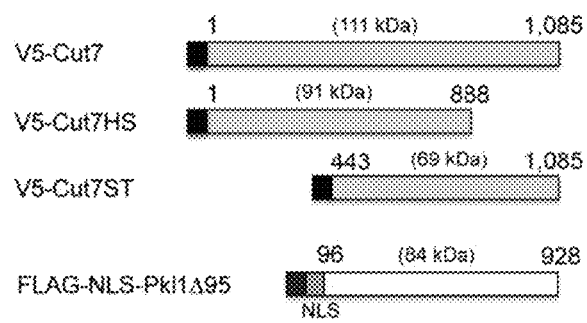
FIGS. 6A-E show that kinesin-5 Cut7 binds the γ-TuRC MTOC. (A) Kinesin-5 and Kinesin-14 constructs used in Fast Protein Liquid Chromatography. V5-tagged Cut7 and two truncation constructs were used, in addition to one FLAG-Pkl1 truncated construct that retains full Pkl1 activity. Cut7 constructs are V5-tagged full length Cut7 (aa 1-1,085), Cut7-Head-Stalk (Cut7HS, aa 1-888) and Cut7-Stalk-Tail (Cut7-ST, aa 443-1,085). (B) Western blot profiles of whole cell extracts fractionated by Superose 6 using FPLC. (C) Western blots of Cut7 constructs immunoprecipitated from whole cell extracts using anti-V5 magnetic beads with empty strain negative controls. (D) Cartoon diagram of 6-His tagged Pkl1 Tail peptide co-immunoprecipitation assay using magnetic beads with His affinity and FPLC fraction 15. (E) Pkl1 Tail peptide co-immunoprecipitation of γ-TuRC core subunits and V5-Cut7ST using a short Pkl1 Tail peptide (PγT). Mutated peptide PγM has significantly reduced interaction with the fission yeast γ-TuRC. The anti-HA antibody detects the HA-tagged γ-TuRC protein Alp4.
Figure 6B:
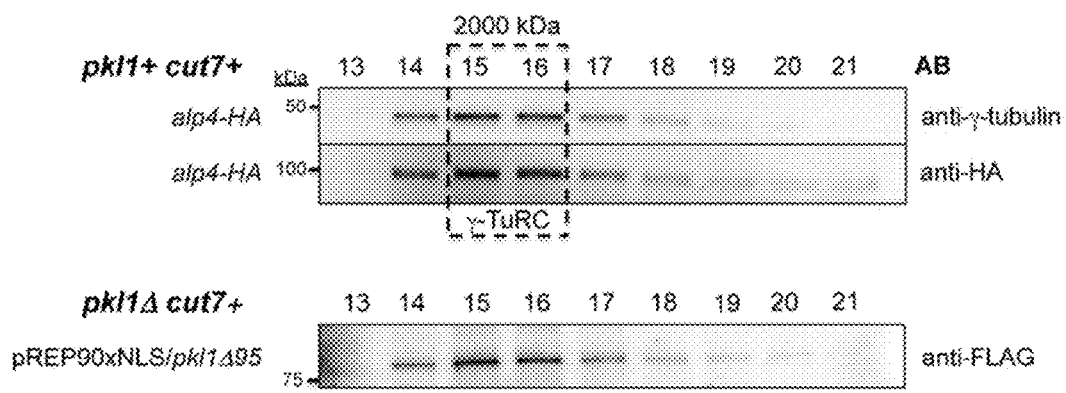
Figure 6C:
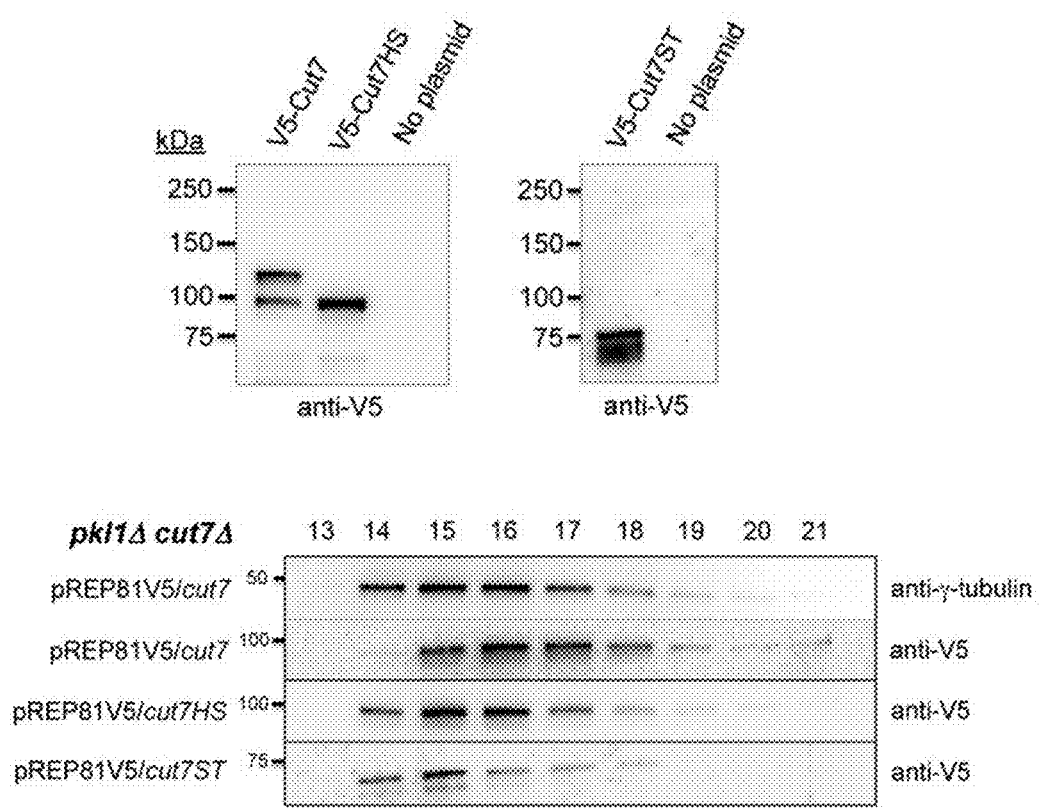
Figure 6D:
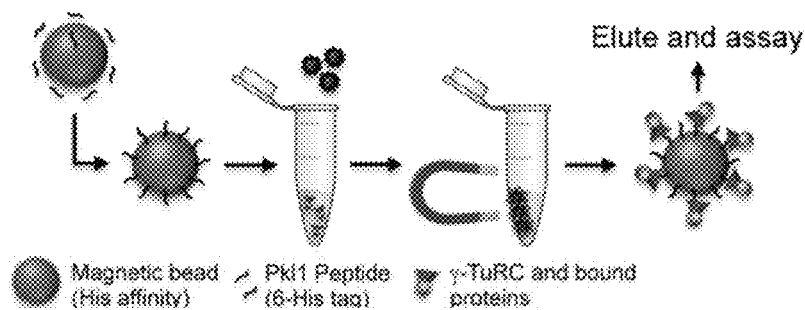
Figure 6E:
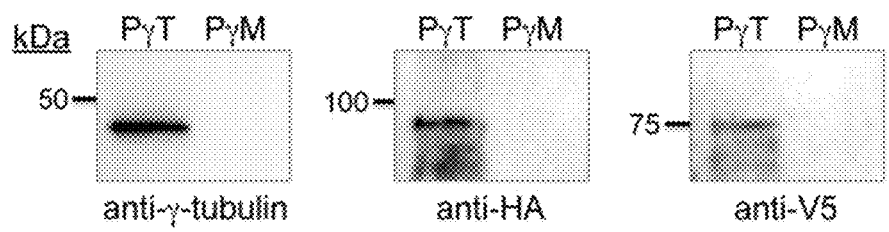
Figure 7A:
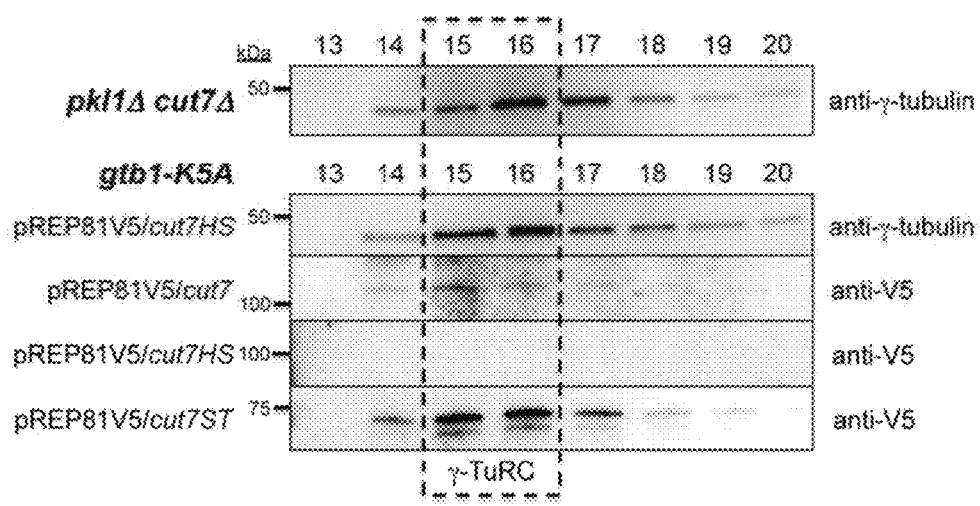
FIGS. 7A-E show that distinct binding of Kinesin-5 Cut7 Motor or BimC domains is required for γ-TuRC association. (A) FPLC profiles of V5-tagged Cut7 and two truncation constructs in γ-tubulin helix 11 mutant gtb1-K5A. (B) Structural model of γ-tubulin-K5A and -PL302 mutants (right) shown with respect to the α-/β-tubulin heterodimer (left). β-tubulin helix 11 is a conserved docking site for Klp Motor domains, and is additionally conserved with fission yeast γ-tubulin helix 11. (C) Fluorescence localization and steady-state expression levels from whole cell extract of full length V5-Cut7 in wild type gtb1 versus the gtb1-K5A mutant. (D) Fluorescence localization of V5-NLS-Cut7ST (Cut7ST, aa 443-1,085) and V5-Cut7HS in the gtb1-K5A strain. (E) Fluorescence localization of four cut7 deletion and BimC site-directed mutagenesis derivatives generated in this study in pkl1Δcut7Δ cells fixed at 36° C. Deletion constructs used are V5-tagged NLS-Cut7-Stalk-Tail, NLS-Cut7-Stalk-Tail$^{22}$ (Cut7ST$^{22}$, Pro to Ser at aa 1,021), NLS-Cut7-Tail (Cut7T, aa 888-1,085) and NLS-Cut7-Tail$^{22}$ (Cut7T$^{22}$, Pro to Ser at aa 1,021). Scale bars are 5 μm.
Figure 7B:
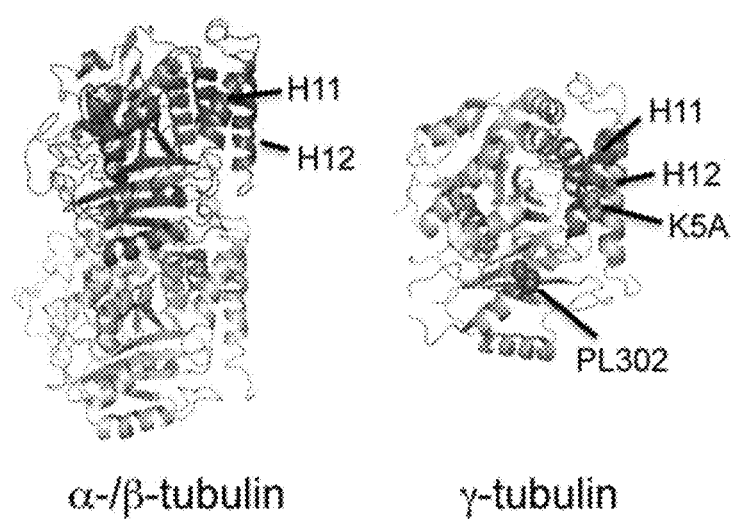
Figure 7C:
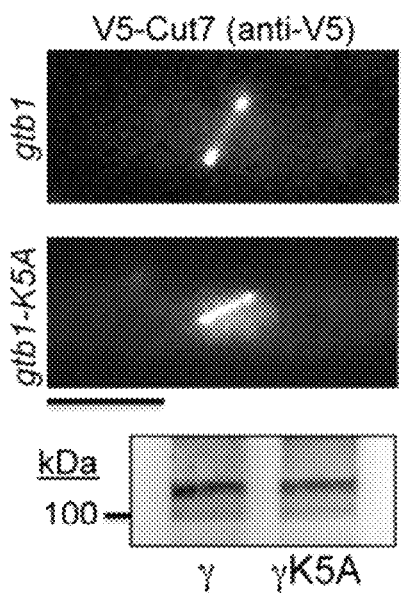
Figure 7D:
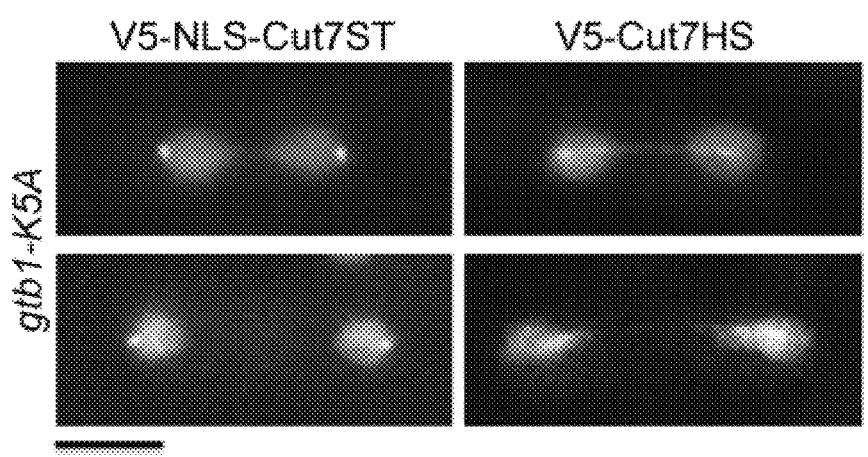
Figure 7E:
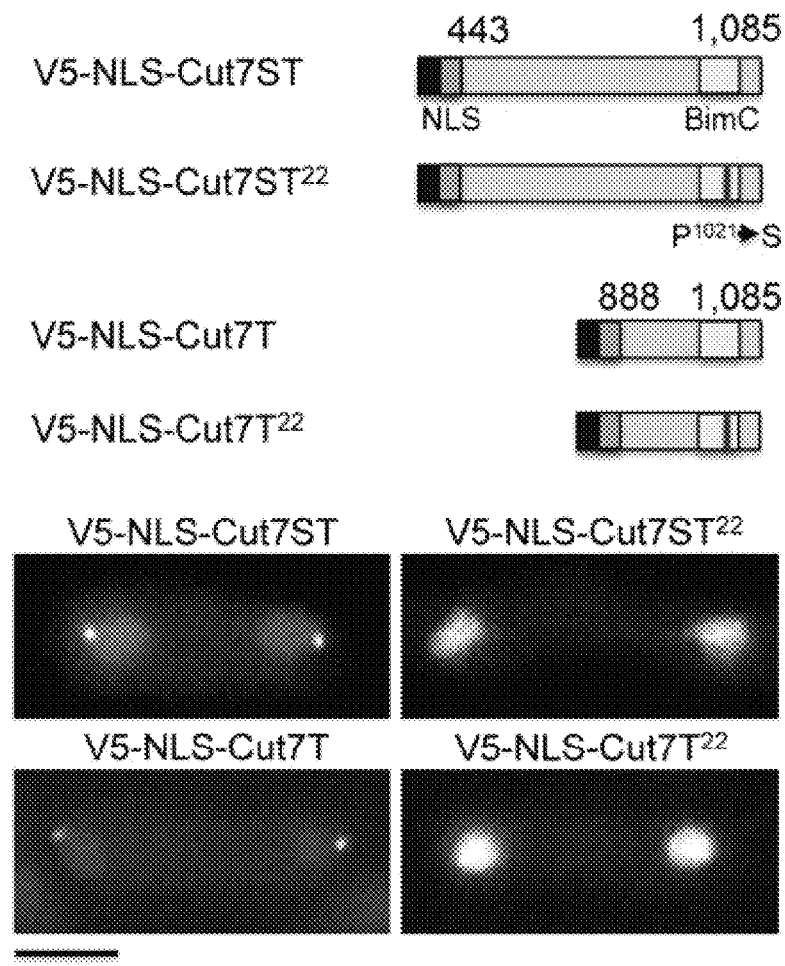

An asymmetric effect on SPB organization with loss of the typical plaque-like appearance at one pole has been observed by TEM analysis of the pkl1Δ strain[20]. Similarly in the pkl1Δ cut7Δ double mutant we observe an asymmetric effect on spindle poles, including altered astral microtubule arrays as previously shown[33]. Here we additionally identify the daughter pole as being primarily affected (FIG. 6). Asymmetry in astral microtubule lengths from opposing poles is observed and orientation is parallel to the spindle axis beginning in early mitosis. Asymmetric astral arrays are observed in 35±6% of pkl1Δ cells and 33±6% of pkl1Δ cut7Δ cells (FIG. 6b; mean±s.e.m., n=200 cells per strain). A small percentage of cells in both strains (8±3% and 6±2%, respectively) exhibit parallel arrays that are symmetric, and the remainder of cells examined have normal appearing astral arrays. Cells without astral microtubules were also observed, but excluded from this analysis. We do not observe protrusions in the nuclear envelope as observed by co-imaging with nuclear envelope and SPB markers shown in FIG. 6C (n=0/57 cells), suggesting that these arrays are cytoplasmic. The septation-initiation network (SIN) protein Cdc7 loads primarily to the daughter pole in mitosis[34,35]. We found that the longer abnormal astral microtubules extend from poles that harbor Cdc7-GFP (68±8% of cells with a signal, n=29 cells) and that this is also the pole with increased thickness (FIG. 6A,D). These data extend the asymmetric SPB disorganization phenotype observed in pkl1Δ cells[20], identifying a role for Pkl1 in maintaining daughter pole organization from γ-TuRC that indirectly alters astral microtubule arrays in the cytoplasm. Further, the data are consistent with daughter pole disorganization contributing to the thicker spindle phenotypes we observe in both pkl1Δ and pkl1Δ cut7Δ mutant cells.

Pkl1Δ and Pkl1Δ Cut7Δ Share Chromosome Segregation Defects.

We monitored chromosome segregation in the double mutant by live cell timelapse fluorescence microscopy and immunocytology of microtubules and DNA as well as mini chromosome loss (FIG. 7). Three types of chromosome segregation defects are present in the double mutant that are unequal segregation, lagging chromosomes and lost chromosomes (FIG. 7A). Compared to wild type cells, the pkl1Δ cut7Δ double mutant strain has increased lagging chromosomes and unequally segregated chromosomes as well as a minor increase in lost chromosomes[36]. However we along with others[20] observe that the efficiency of chromosome segregation is already markedly reduced in the absence of Kinesin-14 Pkl1. Compared to the pkl1Δ cut7Δ double mutant strain, no lost chromosomes are observed in pkl1Δ and unequal segregation is reduced, though lagging chromosomes are prominent. FIG. 7b is a histogram representation of the relative frequencies of these phenotypes in wild type, pkl1Δ single mutant and pkl1Δ cut76 double mutant strains. Shown are frequencies (n=500 cells) for unequal segregation (Type 1; wild type: 0%, pkl1Δ: 7±3%, pkl1Δ cut7Δ: 9±3%, mean±s.e.m.), lagging chromosomes (Type 2; 3±2%, 23±5%, 30±5%) and chromosome loss from the spindle (Type 3; 0%, 0%, 1%). We further quantified chromosome missegregation by monitoring the loss rate of a mini chromosome (cen1-7L) sup3E in the three strains (FIG. 7C). Mini chromosome loss in the pkl1Δ cut7Δ double mutant is greater than wild type (27% increase) but reduced by 5% with respect to pkl1Δ (32%). Our findings on chromosome segregation with pkl1Δ are consistent with previous studies[20] and reveal both rescue (lagging chromosomes) and exacerbation (unequal segregation) of the pkl1Δ phenotype in the double mutant along with the additional lost chromosome phenotype.

In wild type cells, Mad2 monitors proper bipolar attachment of spindle microtubules to the kinetochore (KT), then transitions from KTs to both SPBs coincident with anaphase A onset. In anaphase B, Mad2 becomes asymmetric and makes a subsequent transition from the daughter pole to the equatorial MTOC, but remains asymmetrically localized at the mother pole[26]. We observe Mad2-GFP associated with the lost chromosome that is attached by an intranuclear microtubule (FIG. 7D), similar to what was observed previously with the lost chromosome phenotype[36]. This lost chromosome event occurs in 1% of pkl1Δ cut7Δ cells (n=3/300 cells) and is not observed in pkl1Δ cells. Mad2-GFP was also useful in confirming that the increased spindle microtubule thickness we observe in Type 2 morphologies (FIG. 5B,E) is associated with the daughter pole. By imaging cells with Mad2-GFP and mCherry-Atb2, the increased spindle microtubule thickness extends primarily from the daughter spindle pole that is unmarked or dimly marked by Mad2-GFP in early anaphase B (FIG. 7e), consistent with our Cdc7-GFP data (FIG. 6). Our findings indicate that the chromosome segregation defects in the double mutant strain generally resemble those of pkl1Δ except for the additional presence of the rare lost chromosome phenotype.

An Asymmetric Block on γ-TuRC Nucleation Competency by Pkl1.

We previously demonstrated that Kinesin-14 Pkl1 physically interacts with γ-TuRC in prophase to down regulate its function and oppose bipolar spindle assembly[17,22]. We established an in vivo assay system to examine the impact of elevated levels of Pkl1 in double mutant cells where Kinesin-5 Cut7 is absent (FIG. 8A). Multi copy pkl1 was expressed using the low strength thiamine repressible nmt promoter (pREP81/pkl1). The pkl1Δ cut7Δ cells containing pREP81/pkl1 were grown with or without 5 μg/mL thiamine and were fixed after 17 hours. Cells were stained for α-tubulin and DNA using TAT1 antibody and Hoechst, respectively (FIG. 8A). After thiamine release we observed that 89±9% of cells were arrested with unformed spindles. This frequency was only 6±2% when cells were grown in the presence of thiamine (FIG. 8C, left plot; mean±s.e.m., n=200 cells for both conditions). In cells with unformed spindles, tubulin signal was concentrated near the cell center. We were unable to obtain pkl1Δ cut7Δ cells transformed with pkl1 expressed under a higher strength promoter (pREP90x/pkl1), even under promoter repressing conditions in the presence of thiamine. We additionally performed live cell fluorescence microscopy with GFP-Atb2 (α-tubulin) in the cut7-22 temperature sensitive strain with or without the native pkl1 gene (FIG. 8B). Cells were synchronized by hydroxyurea for four hours, released at the 36° C. restrictive temperature and imaged four hours after release. We observed similar unformed spindles in 82±9% of cells containing Pkl1. The pkl1Δ cut7-22 cells grown similarly exhibit robust spindle assembly (FIG. 8C, right plot; n=200 cells for both conditions), and these data are consistent with the serial growth assays performed with these two strains at 36° C. (FIG. 1B).

Figure 8D:
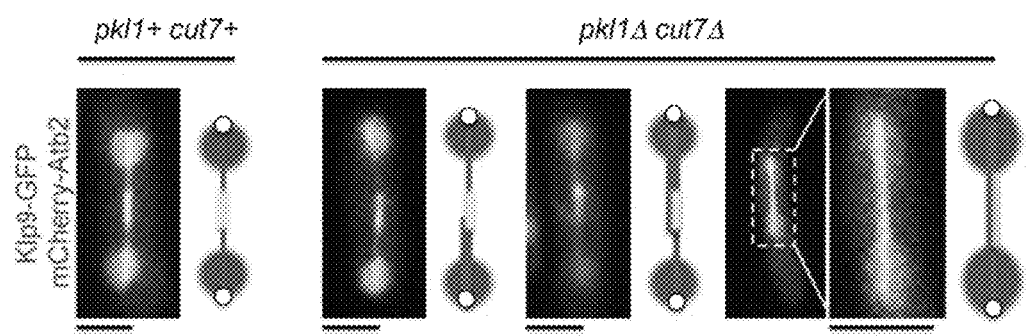
Figure 8E:
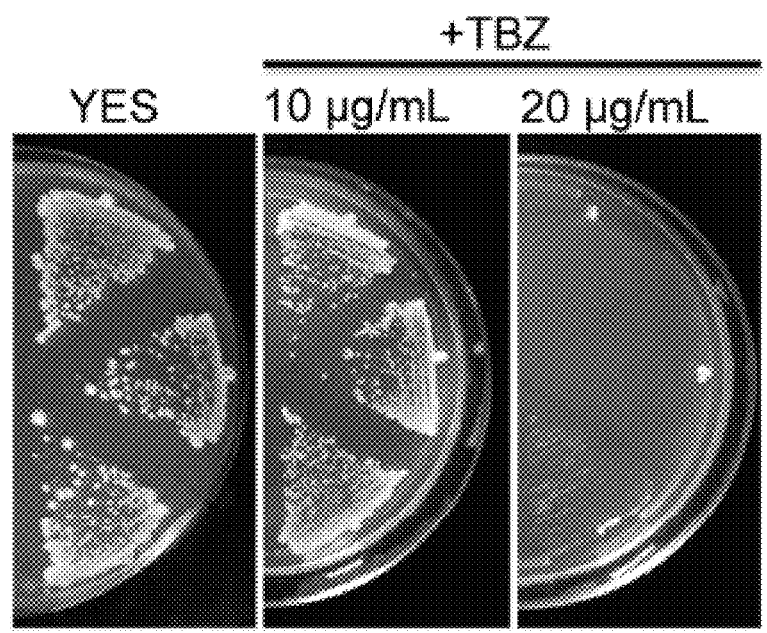

We envision three possible models in which spindle assembly would fail via a spindle pole based mechanism that are based on tubulin seeding at γ-TuRC (FIG. 8D). This includes no addition of tubulin to γ-TuRC, symmetrical addition but without microtubule elongation, or asymmetric addition of tubulin at a single spindle pole. Our data indicate the presence of short microtubules, ruling out model 1. To distinguish between models 2 and 3, we generated the strain [pkl1+ cut7-22 pcp1-GFP mCherry-atb2] to simultaneously visualize poles and microtubules (compare FIG. 8b with 8e). Our data supports model 3. We observe that in 100% of arrested cells where two distinct poles could be identified, the tubulin signal was associated with a single pole (n=25 cells). In vivo nucleation shown by cold depolymerization and reformation of microtubules in FIG. 8f demonstrates that in pkl1Δ cut7Δ cells, γ-TuRC can nucleate both interphase and spindle microtubules, consistent with our other data. Together, the in vivo data here are consistent with our model in which a required role for Cut7 in spindle assembly is to bind γ-TuRC to oppose Pkl1 activity. Therefore of these Klps, Kinesin-14 Pkl1 in fission yeast is the primary negative regulator of γ-TuRC microtubule nucleation.

Kinesin-14 PγTR Peptide Arrests Human Breast Cancer Cells.

All human γ-TuSC proteins are functional in fission yeast[14,15]. This makes fission yeast a suitable model for examining the role and function of these proteins in humans.

Figures 9A, 9B, 9C:
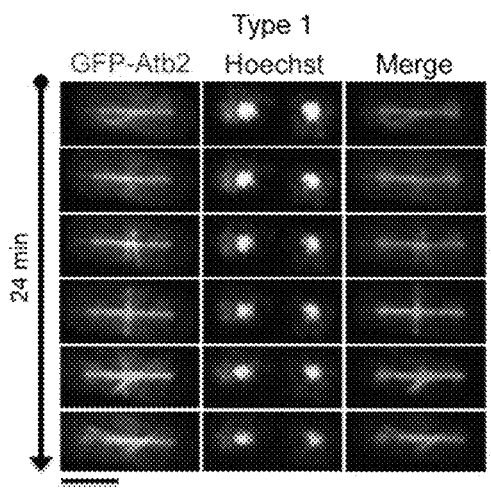
Figure 9D:
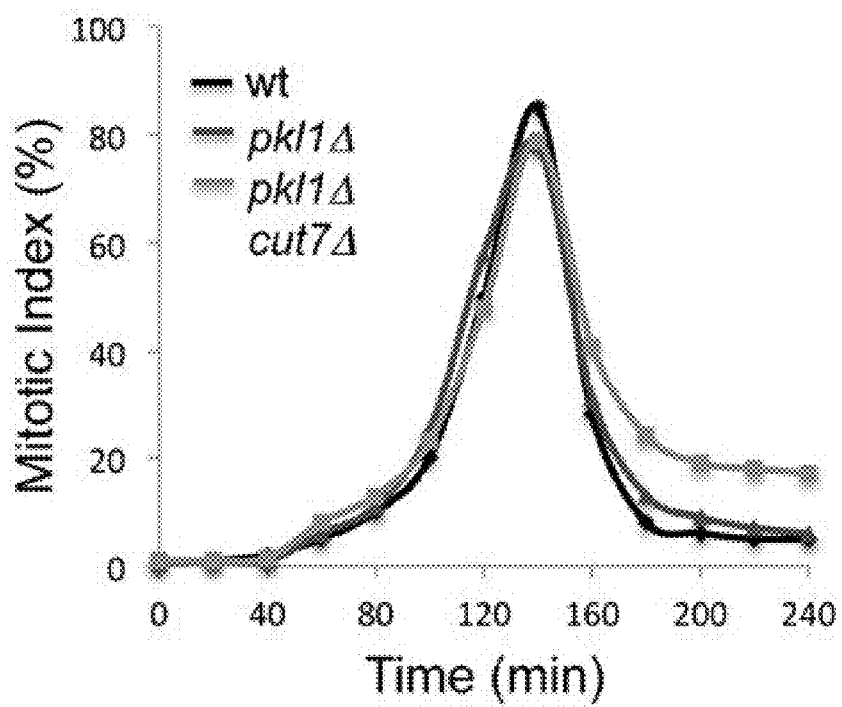

We previously developed biochemical tools in the form of Kinesin-14 Tail peptides[17] that regulate γ-TuRC in vitro and here tested the conserved capability of these peptides to block microtubule nucleation in human MCF-7 breast cancer cells (FIG. 9). By immunocytology in fixed MCF-7 cells we demonstrate that 6-His tagged PγT targets the centrosome (FIG. 9A) and co-localizes with γ-tubulin (FIG. 9B). By microtubule nucleation assays with or without γ-TuRC we also investigated the effect of Kinesin-14 peptides on human γ-TuRC nucleation competency in vitro (FIG. 9C). The control targeting peptide PγT is insufficient to block γ-TuRC microtubule nucleation alone. However, PγTR that contains an additional γ-tubulin binding and regulatory sequence[17] is a potent inhibitor of nucleation. Peptides PγT and PγR (separated TR elements) isolate human γ-TuRC components in vitro similar to their action in fission yeast (FIG. 2e, FIG. 9d). That is, PγT co-immunoprecipitates human GCP2, the yeast Alp4 counterpart, in addition to γ-tubulin, while PγR binds and removes γ-tubulin from the complex[17].

Figures 9F, 9G:
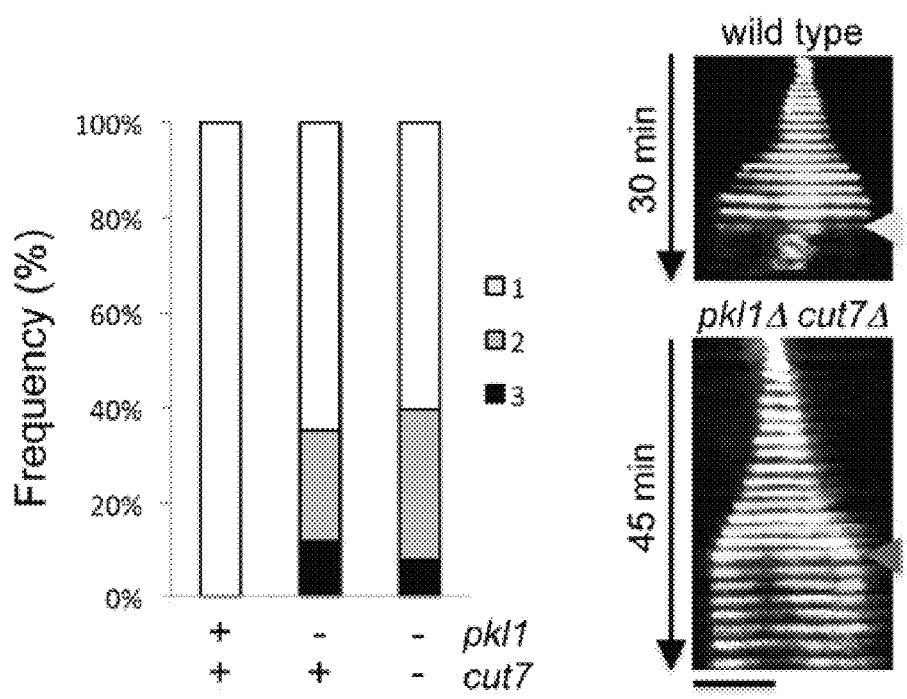
Figure 10A:
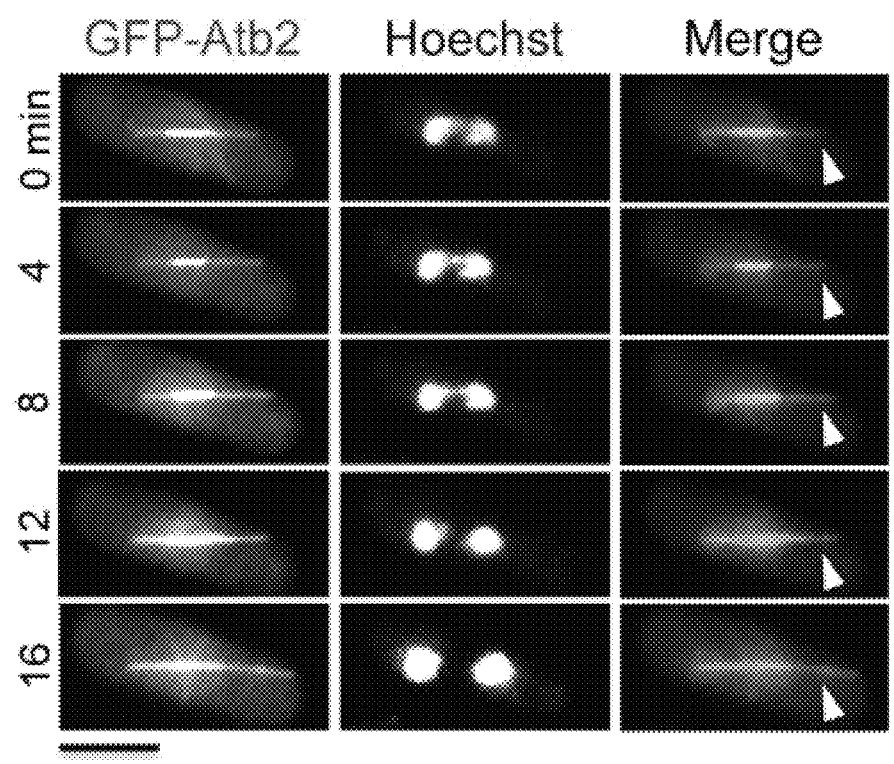
FIGS. 10A-E show changes to the mitotic spindle in the pkl1Δ cut7Δ double mutant strain. (A) Live cell time-lapse fluorescent microscopy series showing an asymmetric astral microtubule array parallel to the mitotic spindle and indicated by a white arrowhead. The microtubules are visualized by GFP-Atb2 (green) and DNA is stained with Hoechst (blue). Separate and merged views. Scale bar is 5 µm. (B) The frequency of parallel symmetric or parallel asymmetric microtubules observed in a native wild type strain versus pkl1Δ single mutant or the pkl1Δ cut7Δ double mutant strains. (C) Spindle pole body (SPB, Pcp1-GFP) and nuclear envelope (NE, P450-GFP) markers in the pkl1Δ cut7Δ cell do not exhibit abnormal NE protrusions beyond either pole (n=0/57 mitotic cells examined). (D) Cdc7-GFP is an asymmetric pole marker that localizes primarily to the daughter pole in mitosis and can be used to identify that pole in a pkl1Δ cut7Δ cell. The asymmetric astral microtubule arrays parallel to the mitotic spindle extend from the pole marked by Cdc7-GFP (white arrowhead, n=27 cells). Scale bar is 5 µm. (E) Frequency of astral microtubules that extend from a pole marked by Cdc7-GFP versus the unmarked pole in a pkl1Δ cut7Δ double mutant (n=45 cells).
Figure 10B:
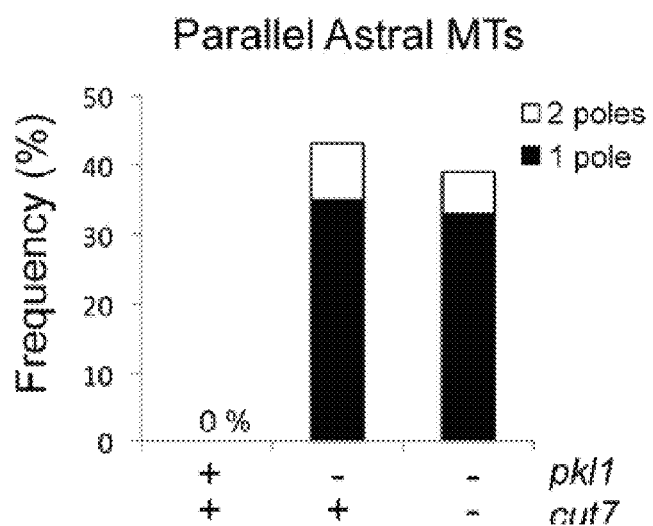
Figure 10C:
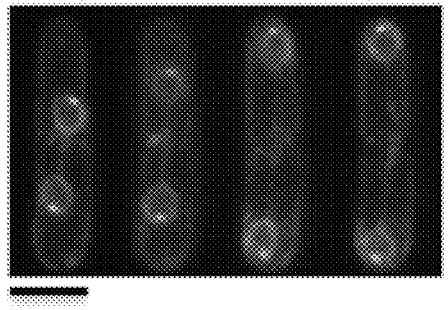
Figure 10D:
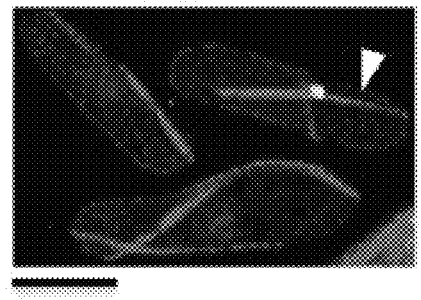
Figure 10E:
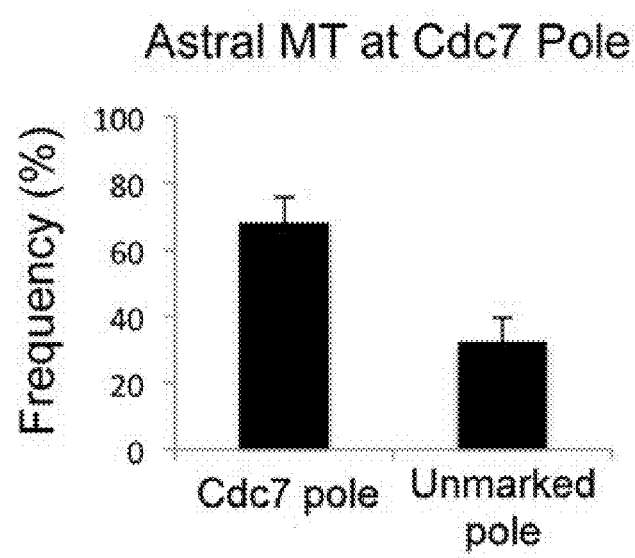
Figure 11A:
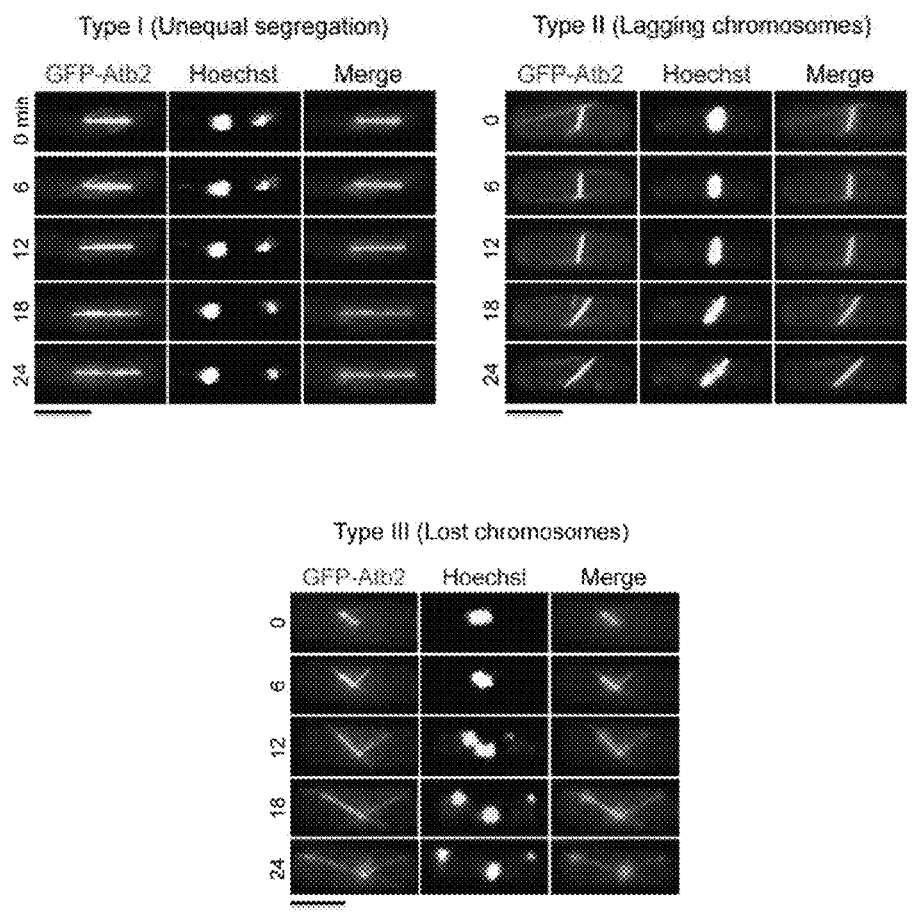
FIGS. 11A-C show that pkl1Δ cut7Δ double mutant cells exhibit defective chromosome segregation. (A) Shown are three live cell time-lapse series of chromosome segregation in pkl1Δ cut7Δ double mutant cells. Microtubules are visualized by GFP-Atb2 (green) and DNA is stained with Hoechst (blue). Scale bar is 5 µm. (B) The frequency of chromosome missegregation phenotypes (types shown in A) in the wild type (pkl1+ cut7+), single mutant (pkl1Δ cut7+) or double mutant (pkl1Δ cut7Δ) strains (n=500 cells/strain). (C) Chromosome loss frequency is measured by a standard mini chromosome loss assay. The frequency was determined for wild type (n=0/1011 cells, 0%), pkl1Δ single mutant (n=316/986, 32%) and the pkl1Δ cut7D double mutant (n=549/2035, 27%).
Figure 11B:
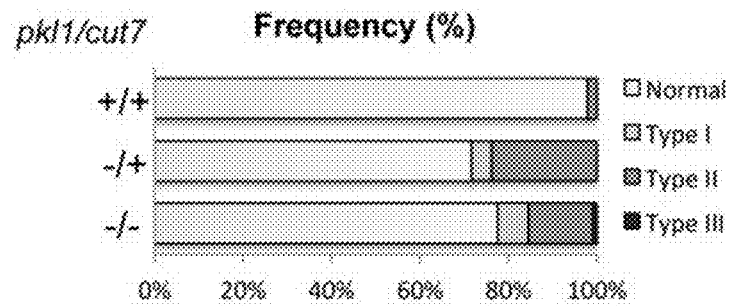
Figure 11C:
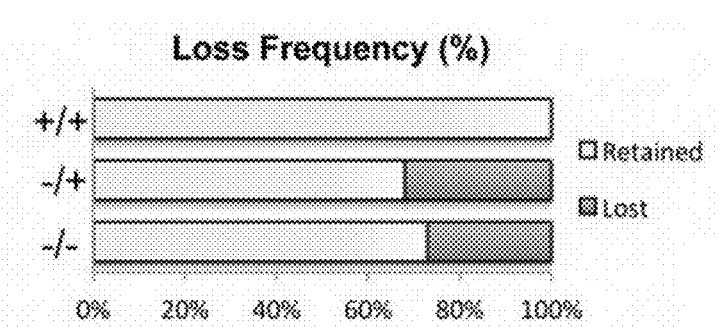
Figure 12A:
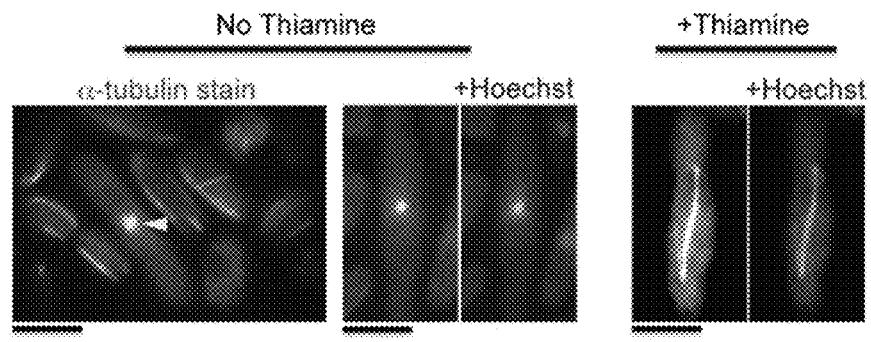
FIGS. 12A-F show that Pkl1 inhibits spindle formation in the pkl1Δ cut7Δ double mutant cells. (A) The presence (repression) or absence (activation) of thiamine can be used to control gene expression of pkl1+ from the pREP81 nmt plasmid promoter and Pkl1 protein levels. Cells were taken from +thiamine plates (repressed gene expression of pkl1+) and used to inoculate media with thiamine (5 µg/ml) or without thiamine. Cells were grown for 17 hours, then fixed with methanol and imaged. A spindle is only observed in cells in which pkl1+ gene expression is repressed (+thiamine, right image). No spindle is observed by α-tubulin staining when pkl1+ is expressed (no thiamine, left image). (B) The presence of Pkl1 (pkl1+) results in no spindle formation in a cut7-22 temperature sensitive mutant strain at 36° C. in which BimC is inactive. Microtubules are visualized by GFP-α-tubulin. Cells were synchronized in growth using standard hydroxyurea block for 4 hours at 27° C., then release into 36° C. growth conditions (n=200 cells/strain). These findings are quantified in (C). In (C) the data reveal that expression of Pkl1 in the absence of Cut7 (cut7Δ) or in the presence of Cut7 that contains an inactive BimC domain (cut7-22) result in unformed spindles. The quantification is significant based on the Student's t-test (mean+/−s.e.m.) that is ***P<0.001. (D) This diagram represents three models for the block in spindle formation tested by our further analysis in (E and F). The models are blocked MTOC nucleation (tubulin seeding) from both of the spindle poles, or MTOC nucleation proceeds but microtubule elongation is blocked, or there is asymmetric blocking of microtubule nucleation. (E) By using the experimental strategy as in (B) along with expression of mCherry-Atb2 (red) to identify tubulin, and Pcp1-GFP to identify the MTOC at spindle poles, the data shows that the third model is correct, in which one pole adds tubulin, while at the second pole no tubulin is added and microtubule nucleation is blocked. Three cells are shown along with zoom images. The arrowheads mark the two spindle pole MTOC sites. (F) By using cold temperature to depolymerize microtubules in the pkl1Δ cut7Δ double mutant strain (that is expressing GFP-Atb2 to visualize microtubules), then moving cells to warm temperature to allow microtubule formation, this experiment demonstrates that there is no block in microtubule nucleation in the absence of both Pkl1 and Cut7. Scale bars are 5 µm.
Figure 12B:
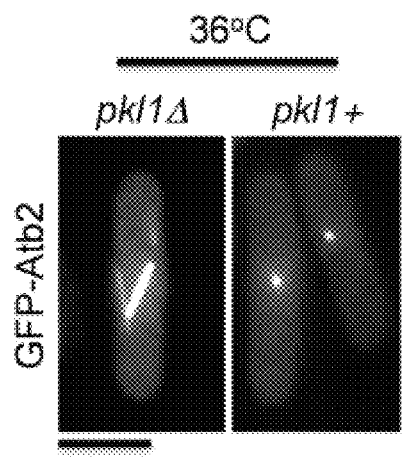
Figure 12C:
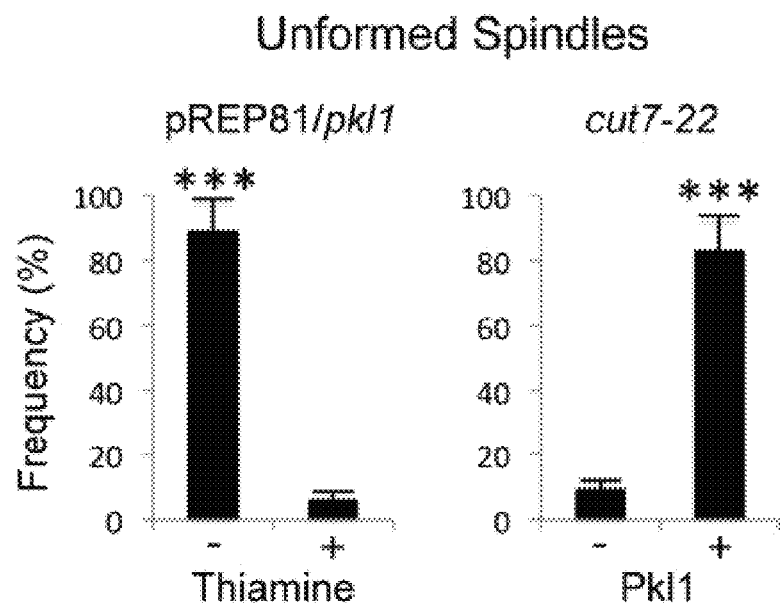
Figure 12D:
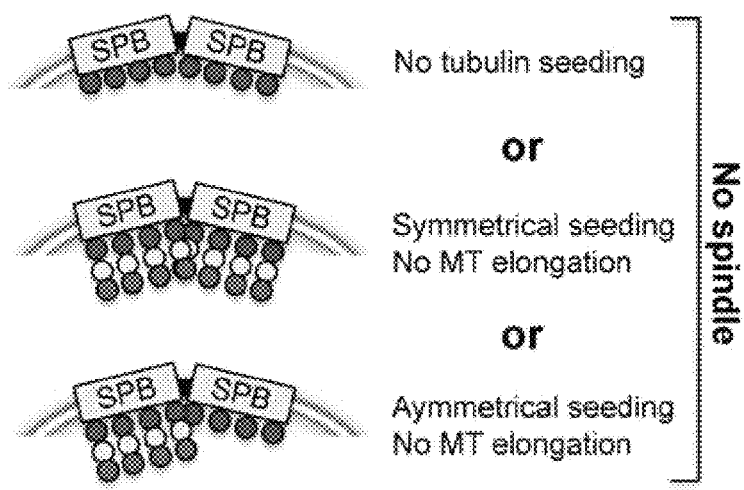
Figure 12E:
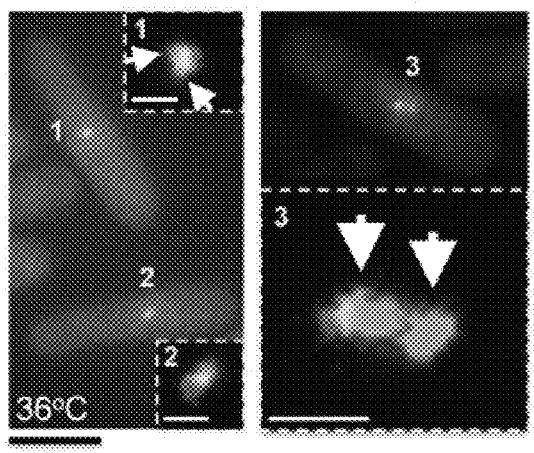
Figure 12F:
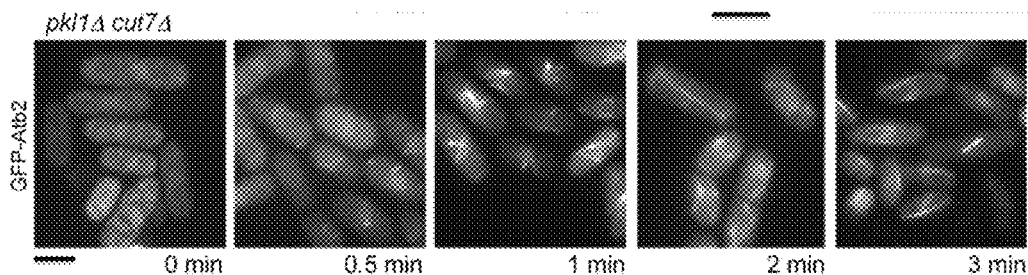
Figure 13A:
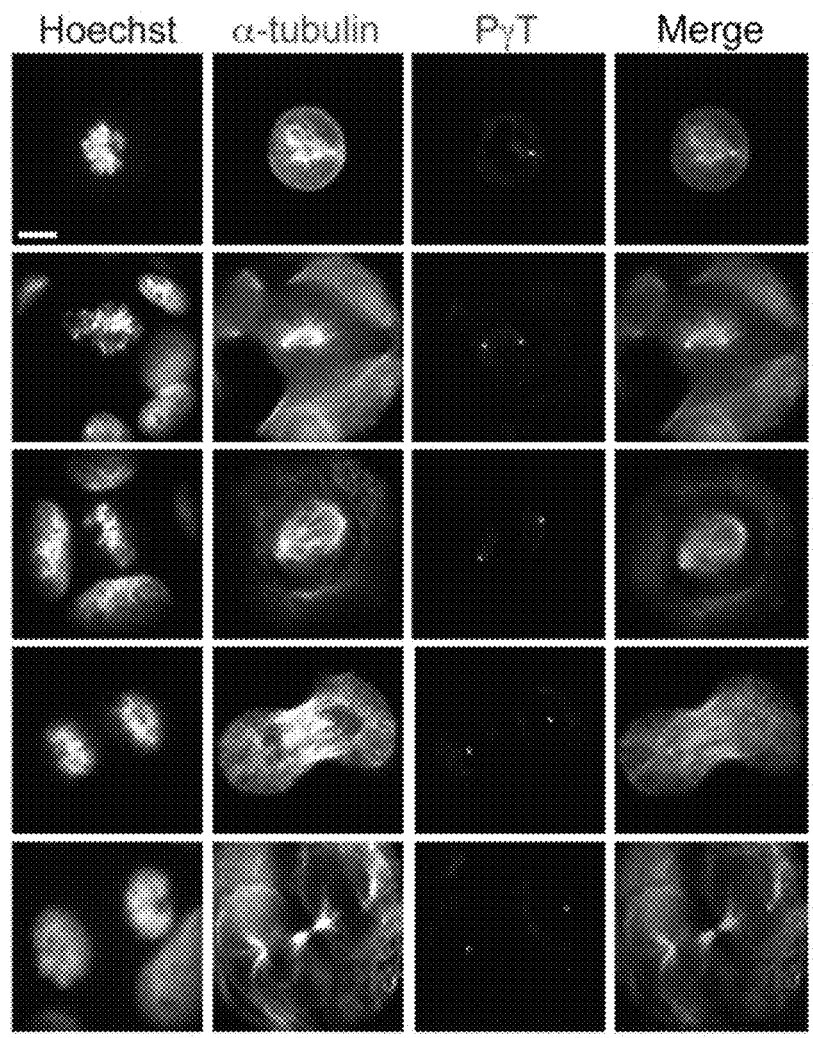
FIGS. 13A-G show conservation of the Kinesin-14 MTOC mechanism using the minimal Pkl1 Tail domain peptides in mammalian rat and human breast cancer lines. (A) Localization of γ-TuRC targeting peptide PγT to centrosomes in fixed human MCF-7 breast cancer cells. DNA is shown in blue (Hoechst), microtubules in green (α-tubulin) and PγT peptide in red. 6-His tagged PγTR was administered before addition of primary antibodies. The PγT lacks catalytic activity to block nucleation but retains targeting to centrosome MTOCs. Various stages of spindle assembly are shown. (B) Co-localization of PγT and MTOC component γ-tubulin at centrosomes in mitotic MCF-7 cells. Scale bars in (A) and (B) are 10 µm. (C) In vitro γ-TuRC microtubule nucleation assays. No γ-TuRC negative controls provide background for spontaneous microtubule formation from tubulin (1.5 µg/ml). All other samples use whole-cell extract from human breast cancer cells. γ-TuRC targeting and regulatory peptide PγTR blocks the γ-TuRC MTOC nucleation. Scale bar, 20 µm (mean±s.d. for number of microtubules per field, n=3 experiments). (D) The magnetic bead assay demonstrates the co-immunoprecipitation of human γ-TuRC core proteins GCP2 and/or γ-tubulin using 6-His-tagged PγT (targeting) peptide and the selective removal of γ-tubulin by the PγR (regulatory) peptide (see FIG. 6D for method). (E) High-magnification images of human breast cancer MCF-7 cells arrested by PγTR (live cell transfection). DNA is in blue (Hoechst), PγTR is in red (top). No spindle formation by α-tubulin staining for microtubules (green). Scale bar, 10 µm. (F) Interphase microtubule arrays in MCF-7 cell containing low levels of PγTR. Scale bar, 10 µm. (G) Mitotic arrest in human breast cancer MCF-7 cells (low-aggressiveness; top images) and MDA-MB-231 cells (high aggressiveness; bottom images) 24 h after transfection with 1 µg (108 µM) of γ-TuRC targeting and regulatory peptide, PγTR. At this time point, 43.3% of MCF-7 cells (681/1,572 cells counted from n=12 fields at ×200) and 27.7% of MDA-MB-231 cells (497/1,732 cells counted from n=12 fields at ×200) were transfected with peptide based on fluorescence staining using the 6-His tag. Of the cells receiving peptide as detected by His-staining, 39% of MCF-7 cells (613/1,572, 90%) and 22.6% of MDA-MB-231 cells (82%) were arrested in mitosis. Left images are Hoechst, and right images are merged Hoechst+PγTR for both cell lines. Scale bars are 50 µm.
Figure 13B:
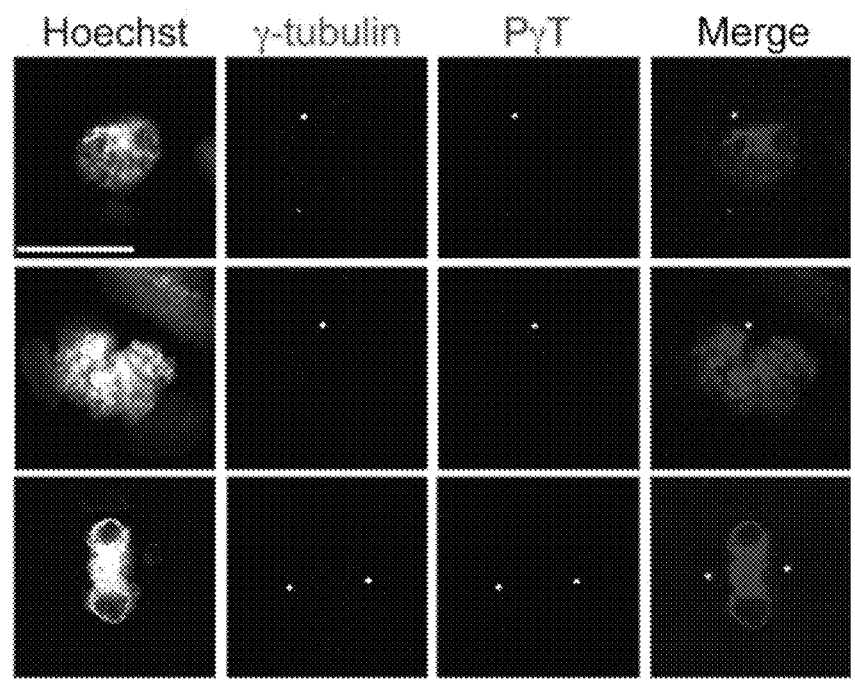
Figure 13C:
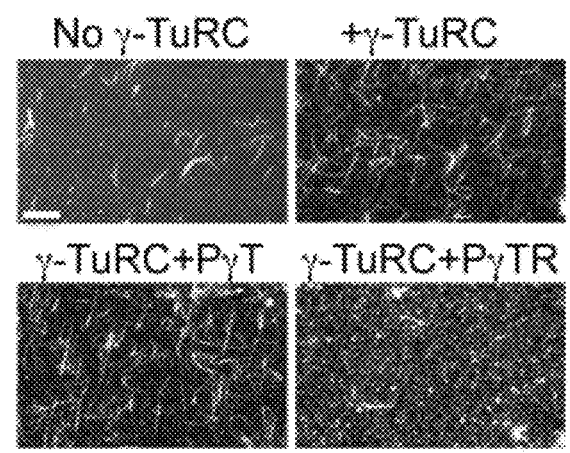
Figure 13C:
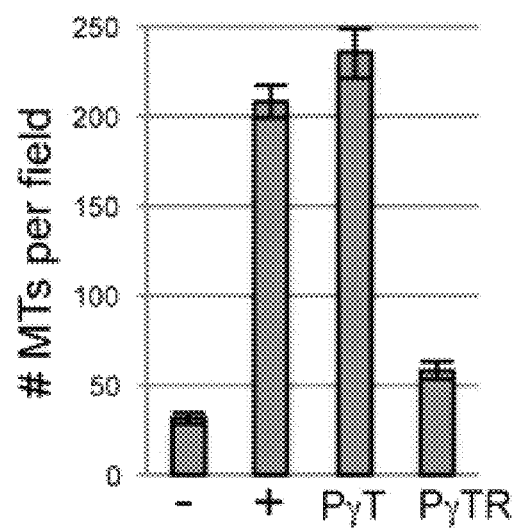
Figure 13D:
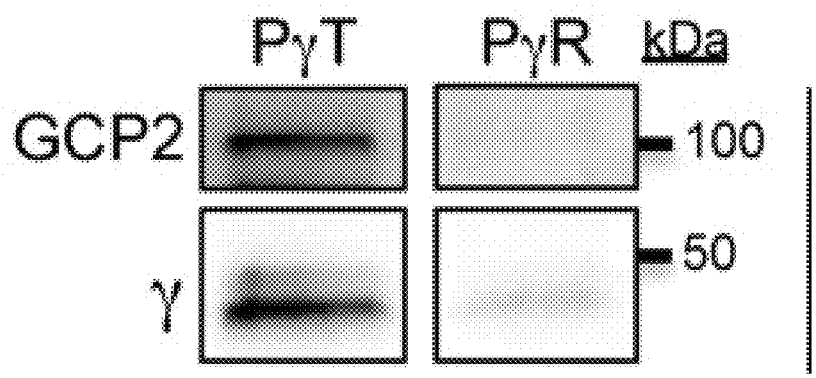
Figure 13E:
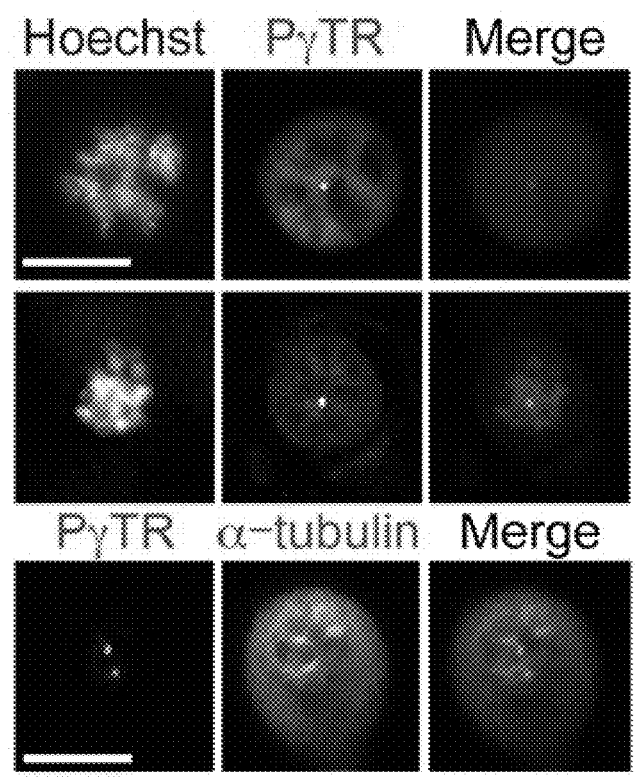
Figure 13F:
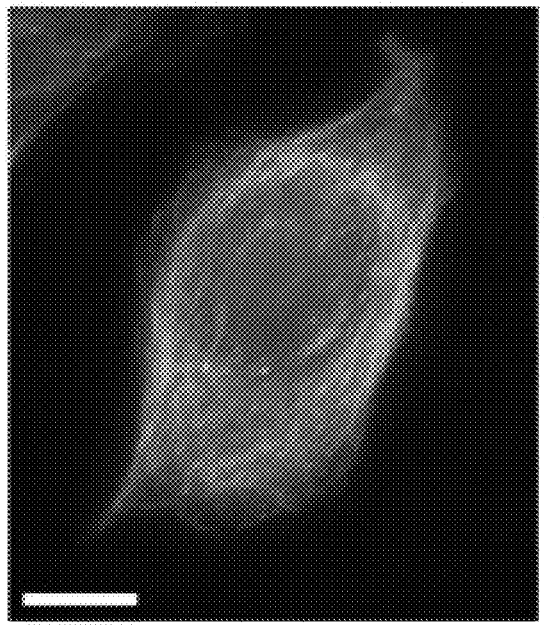
Figure 13G:
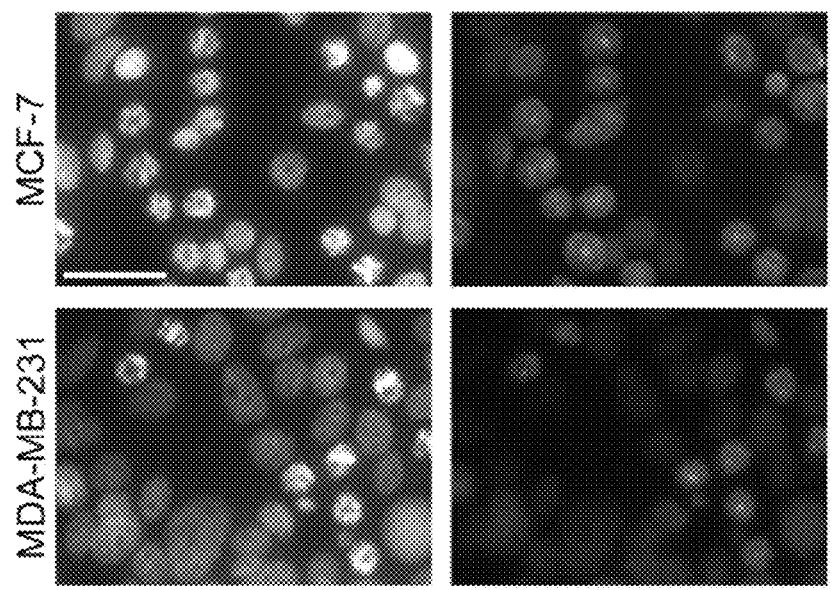
Figure 14A:
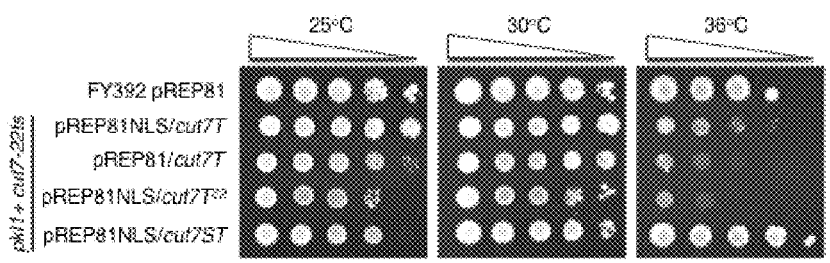
FIGS. 14A-C show that the Kinesin-5 BimC domain is sufficient to counter Kinesin-14. (A) The pkl1+ cut7-22 strain that has an inactive BimC domain that is temperature sensitive (functions at 25° C. but not at 36° C.) was assayed for growth that is indicative of spindle formation and proliferation. At each temperature a 1/10 serial dilution of cells is plated that provides a means to quantify arrested growth. The Cut7 constructs assayed contained only the Tail and Stalk domains and with (cut7T$^{22}$) or without (cut7T, cut7TS) the inactivating mutation in the BimC domain. A nuclear localization sequence (NLS) was provided to target the Cut7 shortened proteins to the nucleus in yeast. In yeast the nuclear envelope remains intact during mitosis and does not break down as in mammalian cells. The assay shows that proliferation (as an assay for nucleation) only occurs with the NLS-cut7T or NLS-cut7TS constructs in which the BimC domain is present and active in the nucleus to allow spindle formation. (B) The same assay as in (A) was used to demonstrate conservation of mechanism with human Kinesin-5. That is the human Kinesin-5 Eg5 can substitute for Cut7 to block Kinesin-14 action and allow nucleation and cell proliferation. (C) The ability of human Eg5 to replace a full deletion of the yeast cut7 gene (cut7Δ) to counter Kinesin-14 is indicated by multiday cell growth.
Figure 14B:
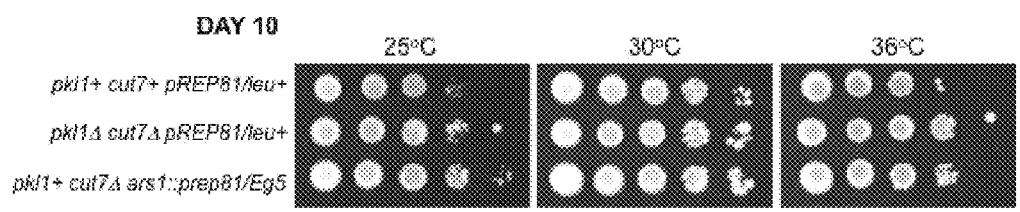
Figure 14C:
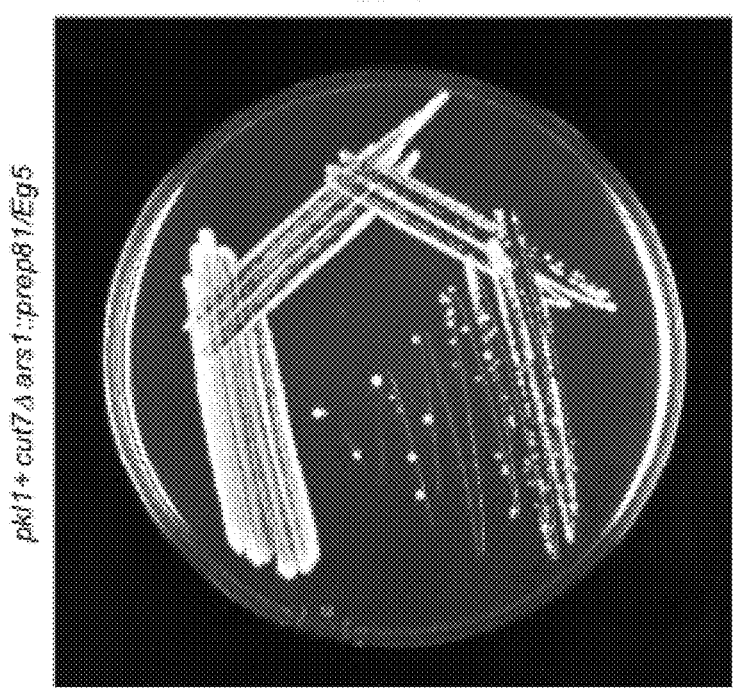
Figure 15A:
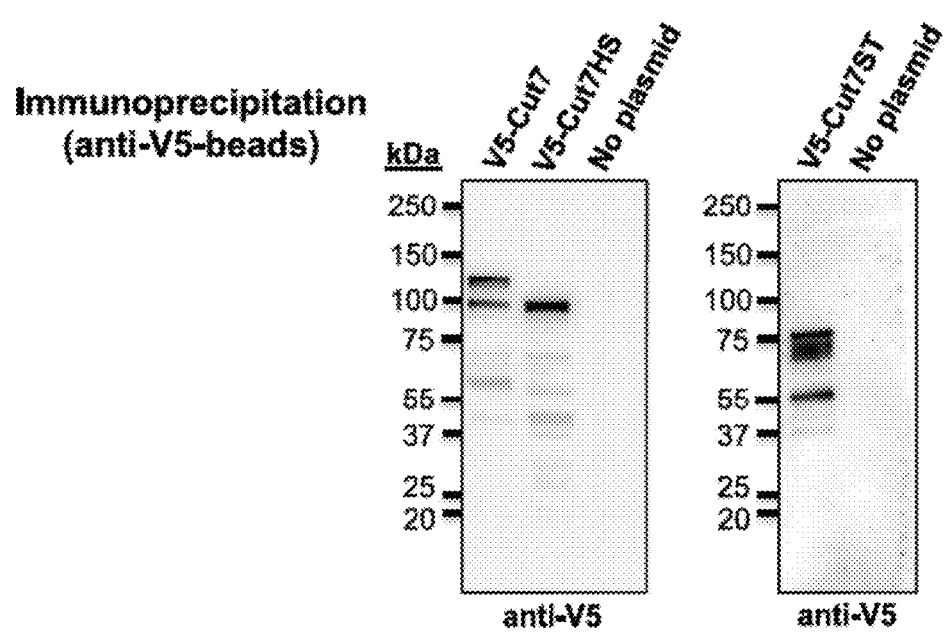
FIGS. 15A-B show that Cut7 full length and truncated forms are stably expressed and that Cut7 can bind to the γ-TuRC MTOC complex with Tail (BimC) or with Motor domain containing constructs. (A) The full length and truncated forms of Cut7 are stably expressed as demonstrated using an antibody against V5 to detect V5-Cut7 full length and V5-Cut7HS (no BimC) or V5-Cut7ST (BimC containing) truncated protein forms expressed from a plasmid. (B) The γ-TuRC MTOC can be size fractionated by Fast Protein Liquid Chromatography (FPLC) on Superpose 6 and is detected by components of the γ-TuRC, such as γ-tubulin or Alp4. A Kinesin-14 Pkl1 minimized Tail domain containing targeting and regulatory elements size fractionates with γ-TuRC (FLAG-tag-Pkl1Δ95) as do the truncated forms of Cut7. This indicates that Cut7 as with Pkl1 can use its motor domain to bind to γ-TuRC as well as its regulatory Tail or BimC domains. Removing motor domain binding to tubulin does not remove BimC binding to γ-TuRC.
Figure 15B:
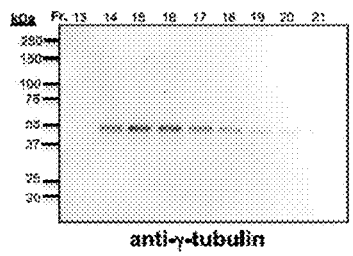
Figure 15B:
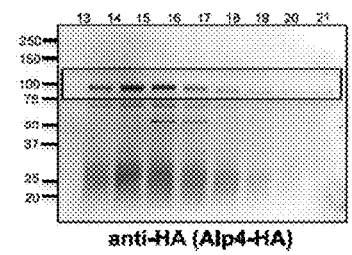
Figure 15B:
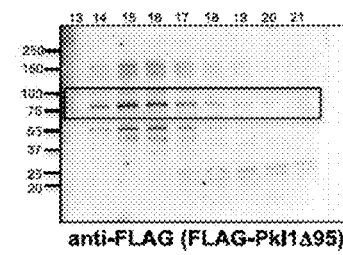
Figure 15B:
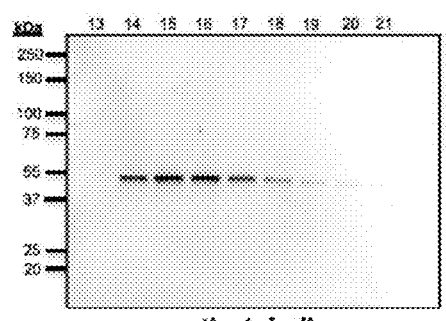
Figure 15B:
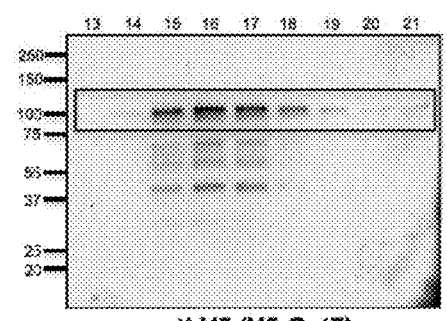
Figure 15B:
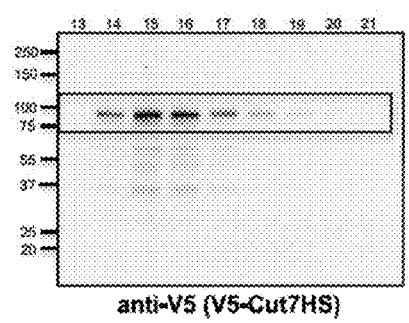
Figure 15B:
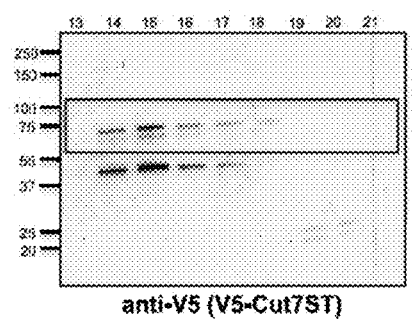

By live cell transfection of human MCF-7 breast cancer cells that exhibit low aggressiveness or MDA-MB-231 cells that are highly aggressive, we show that PγTR is a potent mitotic spindle protein (MSP) class regulator of mitotic arrest (FIG. 9E-G). Cell lines were transfected with 1 μg of 6-His tagged PγTR in 2 mL ($10^8$ μM) using the Chariot system (Active Motif) and fixed after 24 hours. At this time point, 43.3% of MCF-7 cells (681/1,572 cells counted from n=12 fields at 200×) and 27.7% of MDA-MB-231 cells (497/1,732 cells counted from n=12 fields at 200×) were transfected with peptide based on fluorescence staining using the 6-His tag. Of these transfected cells, 39% of MCF-7 cells (613/1,572) and 22.6% of MDA-MB-231 cells were arrested in mitosis. Cells lacking peptide signal did not arrest. Breast cancer lines transfected with a control 6-His hexamer also did not arrest (data not shown), indicating that the His tag does not contribute to the anti-mitotic effect of PγTR. In a small percentage of the populations (4.3% MCF-7; 5.1% MDA-MB-231) with very low but detectable levels of peptide at the centrosome, cells appeared normal (MCF-7 shown in FIG. 9F). In arrested cells, residual clumped microtubules are present but do not appear to extend from centrosomes, suggesting that PγTR has an inhibitory effect on γ-TuRC microtubule nucleation in vivo in human cells. These findings suggest that Kinesin-14 action at γ-TuRC is conserved from the yeast spindle pole body to the human centrosome.

Effective targeting of the MTOC complex to induce mitotic arrest requires (1) binding of Kinesin-14 (or a Kinesin-14 Tail peptide, such as PγTR) to γ-TuRC to block nucleation and (2) blocking the BimC domain of Kinesin-5 to prevent the Kinesin-14 action of (1) to be overridden. In other words, to arrest proliferation, Kinesin-14 should be active and Kinesin-5 should be inactive.

In one embodiment, eukaryotic cells transfected to express the Kinesin-14 Tail peptide, PγTR, can be used to screen for agents that block kinesin-5 BimC. Agents that do not block the Kinesin-5 BimC domain, including Ispinisib, will leave the BimC domain intact, thereby rendering it ineffective to remove the ability of kinesin-5 to counter Kinesin-14 at the MTOC. In other words, in the presence of an active kinesin-5 BimC domain the ability of kinesin-14 to inactivate the MTOC is blocked, promoting spindle formation by the MTOC.

Conversely, an agent that is able to block Kinesin-5 BimC will permit the unimpeded action of Kinesin-14 or a Kinesin-14 Tail peptide such as PγTR to block nucleation at γ-TuRC and ultimately to cause mitotic arrest.

TABLE 1

*Schizosaccharomyces pombe* strains used in this study

| Strain | Genotype |
|---|---|
| FY392 | h– his3-D1 leu1-32 ade6-M210 ura4-D18 |
| JP163 | h+ his3-D1 leu1-32 ura4-D18 ade6-M216 pkl1D::his3+ |
| JP164 | h– his3-D1 leu1-32 ura4-D18 ade6-M216 pkl1D::his3+ |
| JPZ047 | h+ his3-D1 leu1-32 ura4-D18 ade6-M216 pkl1D::his3+ cut4D::ura4+ |
| JPZ048 | h– his3-D1 leu1-32 ura4-D18 ade6-M216 pkl1D::his3+ cut4D::ura4+ |
| JP181 | h+ his3-D1 leu1-32 ura4-D18 ade6-M216 cut4-22ts |
| JP183 | h+ his3-D1 leu1-32 ura4-D18 ade6-M216 pkl1D::his3+ cut4-22ts |
| JPZ049 | h– his3-D1 leu1-32 ade6-M210 ura4-D18 [a rs1::p rep41GFP/atb2] |
| JPZ050 | h+ his3-D1 leu1-32 ura4-D18 ade6-M216 pkl1D::his3+ [ars1::p rep41GFP/atb2] |
| JPZ051 | h+ his3-D1 leu1-32 ura4-D18 ade6-M216 pkl1D::his3+ cut4D::ura4+[ars1::p |
| JPZ052 | h+ his3-D1 leu1-32 ura4-D18 ade6-M216 cut4-22ts [ars1::p rep41GFP/atb2] |

TABLE 1-continued

*Schizosaccharomyces pombe* strains used in this study

| Strain | Genotype |
|---|---|
| JPZ053 | h+ his3-D1 leu1-32 ura4-D18 ade6-M216 pkl1D::his3+ cut4-22ts [ars1::p |
| JPZ054 | h+ his3-D1 leu1-32 ura4-D18 ade6-M216 cut4-22ts [ars1::pJPGFP/gtb1] |
| JPZ055 | h+ his3-D1 leu1-32 ura4-D18 ade6-M216 pkl1D::his3+ cut4-22ts |
| JP114 | h− his3-D1 leu1-32 ura4-D18 ade6-M210 pcp1-GFP::G418$_R$ |
| JP265 | h− his3-D1 leu1-32 ura4-D18 pcp1-GFP::G418$_R$ pkl1D::his3+ |
| JPZ056 | his3-D1 leu1-32 ura4-D18 pcp1-GFP-G418$_R$ pkl1D::his3+ cut4D::ura4+ |
| JPZ057 | h− his3-D1 leu1-32 ura4-D18 pcp1-GFP::G418$_R$ [ars1::p rep81GFP/P450] |
| JPZ058 | h− his3-D1 leu1-32 ura4-D18 pcp1-GFP::G418$_R$ pkl1D::his3+ [ars1::p |
| JPZ059 | h+ his3-D1 leu1-32 ura4-D18 pcp1-GFP::G418$_R$ pkl1D::his3+ cut4D::ura4+ [ars1::p |
| 1PZ060 | h− his3-D1 leu1-32 ura4-D18 pcp1-GFP::G418$_R$ [ars1::p rep41mCherry/atb2] |
| JPZ061 | h− his3-D1 leu1-32 ura4-D18 pcp1-GFP::G418$_R$ pkl1D::his3+ [ars1::p |
| JPZ062 | his3-D1 leu1-32 ura4-D18 pcp1-GFP::G418$_R$ pkl1D::his3+ cut4D::ura4+ [ars1::p |
| JPZ063 | h+ his3-D1 leu1-32 ura4-D18 ade6-M216 pcp1-GFP::G418$_R$ pkl1D::his3+ |
| JPZ064 | h+ his3-D1 leu1-32 ura4-D18 ade6-M216 pkl1D::his3+ cut4D::ura4+ |
| JP81 | h− leu1-32 ura4-D18 ade6-404 [pSp(cen1-4L)sup3E::ura4+] |
| JPZ065 | leu1-32 ura4-D18 ade6-404 pkl1D::his3+ [pSp(cen1-4L)sup3E::ura4+] |
| JPZ066 | leu1-32 ura4-D18 ade6-404 pkl1D::his3+ cut4D::ura4+ [pSp(cen1-4L)sup3E::ura4+] |
| JP113 | h+ leu1-32 ura4-D18 ade6-M210 mad2D::ura4+ |
| JPZ067 | his3-D1 leu1-32 ura4-D18 pkl1D::his3+ cut4D::ura4+ mad2D::ura4+ |
| ColP16 | h− leu1-32 mad2-eGFP::ura4+ |
| JP113 | leu1-32 pkl1D::his3+ mad2-eGFP::ura4+ |
| JPZ068 | leu1-32 pkl1D::his3+ cut4D::ura4+ mad2-eGFP::ura4+ |
| JPZ069 | leu1-32 pkl1D::his3+ cut4D::ura4+ mad2-eGFP::ura4+ [ars1::prep41mCherry/atb2] |
| JP136 | h− leu1-32 ura4-D18 ade6-M210 gtb1-PL302 |
| JPZ070 | leu1-32 ura4-D18 ade6-M210 gtb1-PL302 pkl1D::his3+ cut4D::ura4+ |
| JPZ071 | leu1-32 ura4-D18 ade6-M210 gtb1-PL302 pkl1D::his3+ cut4D::ura4+ |
| JP129 | his4-336/his4− leu1-32/1eu1-32 ura4-D18/ura4-D18 ade6-M210/ade6-M216 |
| JPZ072 | his4− leu1-32 ura4-D18 gtb1D::his4+ [ars1::prep81GFP/gtb1-K5A] |
| JPZ073 | his4− leu1-32 ura4-D18 gtb1D::his4+ [ars1::prep81GFP/gtb1-K5A] pkl1D::his3+ |
| JPZ074 | his4− leu1-32 ura4-D18 gtb1D::his4+ [ars1::prep81GFP/qtb1-K5A1 cut4D::ura4+ |
| JPZ075 | his4− leu1-32 ura4-D18 gtb1D::his4+ [ars1::prep42/gtb1-K5A] [pREP81FLAG/pkl1] |
| JPZ076 | his4− leu1-32 ura4-D18 gtb1D::his4+ [ars1::prep42/gtb1-K5A] [pREP81V5 cut4] |
| JPZ077 | his4− leu1-32 ura4-D18 gtb1D::his4+ [ars1::prep42/gtb1-K5A] [pREP81V5/cut4- |
| JPZ078 | his4− leu1-32 ura4-D18 gtb1D::his4+ [ars1::prep42/gtb1-K5A] [pREP81V5/cut4-ST] |
| JPZ079 | h+ his3-D1 leu1-32 ura4-D18 ade6-M216 pkl1D::his3+ [pREP81FLAG/pkl1] |
| JPZ080 | h+ his3-D1 leu1-32 ura4-D18 ade6-M216 pkl1D::his3+ [pREP90x/pkl1D95NLS] |
| JPZ081 | h+ his3-D1 leu1-32 ura4-D18 ade6-M216 pkl1D::his3+ cut4D::ura4+ |
| JPZ082 | h+ his3-D1 leu1-32 ura4-D18 ade6-M216 pkl1D::his3+ cut4D::ura4+ |
| JPZ083 | h+ his3-D1 leu1-32 ura4-D18 ade6-M216 pcp1-GFP::G418$_R$ pkl1D::his3+ cut4D::ura4+ [pREP81FLAG/pkl1] |
| JPZ084 | h+ his3-D1 leu1-32 ura4-D18 ade6-M216 pkl1D::his3+ [pREP81V5/cut4] |
| JPZ085 | h+ his3-D1 leu1-32 ura4-D18 ade6-M216 pkl1D::his3+ cut4D::ura4+ |
| JPZ086 | h+ his3-D1 leu1-32 ura4-D18 ade6-M216 pkl1D::his3+ cut4D::ura4+ |
| JPZ087 | h+ his3-D1 leu1-32 ura4-D18 ade6-M216 pkl1D::his3+ cut4D::ura4+ |
| JPZ088 | h+ his3-D1 leu1-32 ura4-D18 ade6-M216 pkl1D::his3+ cut4D::ura4+ |
| JPZ089 | h+ his3-D1 leu1-32 ura4-D18 ade6-M216 pkl1D::his3+ cut4D::ura4+ |
| JPZ090 | h+ his3-D1 leu1-32 ura4-D18 ade6-M216 pkl1D::his3+ cut4D::ura4+ |
| JPZ091 | h+ his3-D1 leu1-32 ura4-D18 ade6-M216 pkl1D::his3+ cut4D::ura4+ [pREP81V5NLS/cut4T$^{22}$] |
| LV15 | h− leu1-32 alp4-HI::G418$_r$ |
| JPZ092 | h− leu1-32 alp4-HI::G418$_r$ [pREP81V5/cut4] |
| JPZ093 | h− leu1-32 alp4-HI::G418$_r$ [pREP81V5NLS/cut4ST] |
| JP272 | h− his3-D1 leu1-32 ura4-D18 ade6-M210 klp9-GFP::ura4+ |
| JP270 | h− his3-D1 leu1-32 ura4-D18 ade6-M210 pkl1D::his3+ klp9-GFP::ura4+ |
| JPZ094 | his3-D1 leu1-32 ura4-D18 pkl1D::his3+ cut4D::ura4+ klp9-GFP::ura4+ |
| JPZ095 | his3-D1 leu1-32 ura4-D18 pkl1D::his3+ cut4D::ura4+ klp9-GFP::ura4+ |
| JPZ096 | h− his3-D1 leu1-32 ura4-D18 pkl1D::his3+ [pREP82GFP/klp9] |
| JPZ097 | his3-D1 leu1-32 ura4-D18 cdc4-GFP::ura4+ pkl1D::his3+ cut4D::ura4+ |
| JPZ098 | his3-D1 leu1-32 ura4-D18 cut4-22ts pcp1-GFP::G418$_R$ [ars1::p |

REFERENCES

1. Rieder, C. & Khodjakov, A. Mitosis through the microscope: advances in seeing inside live dividing cells. *Science* 300, 91-96 (2003).

2. Riehlman, T. R., Olmsted, Z. T. & Paluh, J. L. *The Nanobiotechnology Handbook. Chapter 4: Molecular Motors*. CRC Press (2012). ISBN 9781439838693.

3. Manchado, E., Guillamot, M. & Malumbres, M. Killing cells by targeting mitosis. *Cell Death Differ.* 19, 369-377 (2012).

4. Pickett-Heaps, J. D. The evolution of the mitotic apparatus: an attempt at comparative ultrastructural plant cytology in dividing plant cells. *Cytobios.* 1, 257-280 (1969).

5. Oakley, C. E. & Oakley, B. R. Identification of gamma-tubulin, a new member of the tubulin superfamily encoded by mipA gene of *Aspergillus nidulans*. *Nature* 338, 662-664 (1989).

6. Stearns, T., Evans, L. & Kirschner, M. γ-tubulin is a highly conserved component of the centrosome. *Cell* 65, 625-636 (1991).

7. Moritz, M. et al. Structure of the γ-tubulin ring complex: a template for microtubule nucleation. *Nat. Cell Biol.* 2, 365-370 (2000).
8. Wiese, C. & Zheng, Y. Microtubule nucleation: γ-tubulin and beyond. *J. Cell Sci.* 119, 4143-4153 (2006).
9. Lüders, J. & Stearns, T. Microtubule-organizing centres: a re-evaluation. *Nat. Rev. Mol. Cell Biol.* 8, 161-167 (2007).
10. Nogales, E., Wolf, S. G. & Downing, K. H. Structure of the α/β-tubulin dimer by electron crystallography. *Nature* 391, 199-203 (1998).
11. Aldaz, H., Rice, L. M., Stearns, T. & Agard, D. A. Insights into microtubule nucleation from the crystal structure of human γ-tubulin. *Nature* 435, 523-527 (2005).
12. Guillet, V. et al. Crystal structure of γ-tubulin complex protein GCP4 provides insight into microtubule nucleation. *Nat. Struc. Mol. Biol.* 18, 915-921 (2011).
13. Kollman, J. M. et al. The structure of the γ-tubulin small complex: implications of its architecture and flexibility for microtubule nucleation. *MBoC* 19, 207-215 (2008).
14. Horio, T. & Oakley, B. R. Human γ-tubulin functions in fission yeast. *J. Cell Biol.* 126, 1465-1473 (1994).
15. Riehlman, T. R. et al. Functional replacement of fission yeast γ-tubulin small complex proteins Alp4 and Alp6 by human GCP2 and GCP3. *J. Cell Sci.* 126, 4406-4413 (2013).
16. Masuda, H., Mori, R., Yukawa, M. & Toda, T. Fission yeast MOZART/Mzt1 is an essential γ-tubulin complex component for complex recruitment to the microtubule organizing center, but not its assembly. *MBoC* 24, 2894-2906 (2013).
17. Olmsted, Z. T. et al. Kinesin-14 Pkl1 targets γ-tubulin for release from the γ-tubulin ring complex (γ-TuRC). *Cell Cycle* 12, 842-848 (2013).
18. Pidoux, A. L., LeDizet, M., & Cande, W. Z. Fission yeast pkl1 is a kinesin-related protein involved in mitotic spindle function. *MBoC* 7, 1639-1655 (1996).
19. Saunders, W., Hornack, D., Lengyel, V. & Deng, C. The *Saccharomyces cerevisiae* kinesin-related motor Kar3p acts a preanaphase spindle poles to limit the number and length of cytoplasmic microtubules. *J. Cell Biol.* 137, 417-431 (1997).
20. Grishchuk, E. L., Spiridonov, I. S. & McIntosh, J. R. Mitotic chromosome biorientation in fission yeast is enhanced by dynein and a minus-end directed, kinesin-like protein. *MBoC* 18, 2216-2225 (2007).
21. Cai, S., Weaver, L. N., Ems-McClung, S. C. & Walczak, C. E. Proper organization of microtubule minus-ends is needed for midzone stability and cytokinesis. *Curr. Biol.* 20, 880-885 (2010).
22. Rodriguez, A. S. et al. Protein complexes at the microtubule organizing center regulate bipolar spindle assembly. *Cell Cycle* 7, 1246-1253 (2008).
23. Simeonov, D. R. et al. Distinct kinesin-14 mitotic mechanisms in spindle bipolarity. *Cell Cycle* 8, 3563-3575 (2009).
24. Paluh, J. L. et al. A mutation in γ-tubulin alters microtubule dynamics and organization and is synthetically lethal with the Klp Pkl1p. *MBoC* 11, 1225-1239 (2000).
25. Tange, Y., Fujita, A., Toda, T. & Niwa, O. Functional dissection of the γ-tubulin complex by suppressor analysis of gtb1 and alp4 mutations in *Schizosaccharomyces pombe*. *Genetics* 167, 1095-1107 (2004).
26. Mayer, C., Filopei, J., Batac, J., Alford, L. & Paluh, J. L. An extended anaphase signaling pathway for Mad2p includes microtubule organizing center proteins and multiple motor transitions. *Cell Cycle* 5, 1456-1463 (2006).
27. Hagan, I. & Yanagida, M. Novel potential mitotic motor protein encoded by the fission yeast cut7+ gene. *Nature* 347, 563-566 (1990).
28. Fu, C. et al. Phosphoregulated interaction between Kinesin-6 Klp9 and microtubule bundler Ase1p promotes spindle elongation. *Dev. Cell* 17, 257-267 (2009).
29. Drummond, D. R. & Hagan, I. M. Mutations in the bimC box of Cut7 indicate divergence of regulation within the bimC family of kinesin related proteins. *J. Cell Sci.* 111, 853-865 (1998).
30. Heck, M. M. S. et al. The Kinesin-like Protein KLP61F Is Essential for Mitosis in *Drosophila*. *J. Cell Biol.* 123, 665-679 (1993).
31. Lawrence, C. J. et al. A standardized kinesin nomenclature. *J. Cell Biol.* 167, 19-22 (2004).
32. Enos, A. P. & Morris, N. R. Mutation of a gene that encodes a kinesin-like protein blocks nuclear division in *A. nidulans*. *Cell* 60, 1019-1027 (1990).
33. Syrovatkina, V., Fu, C. & Tran, P. T. Antagonistic spindle motors and MAPs regulate metaphase spindle length and chromosome segregation. *Curr. Biol.* 23, 2423-2429 (2013).
34. Schmidt, S., Sohrmann, M., Hofmann, K., Woollard, A. & Simanis, V. The Spg1p GTPase is an essential, dosage-dependent inducer of septum formation in *Schizosaccharomyces pombe*. *Genes Dev.* 11, 1519-1534 (1997).
35. Grallert, A., Krapp, A., Bagley, S., Simanis, V. & Hagan, I. M. Recruitment of NIMA kinase shows that maturation of the *S. pombe* spindle-pole body occurs over consecutive cell cycles and reveals a role for NIMA in modulating SIN activity. *Genes Dev.* 18, 1007-1021 (2004).
36. Gachet, Y. et al. Sister kinetochore recapture in fission yeast occurs by two distinct mechanisms, both requiring Dam1 and Klp2. *MBoC* 19, 1646-1662 (2008).
37. Hagan, I. & Yanagida, M. Kinesin-related cut7 protein associates with mitotic and meiotic spindles in fission yeast. *Nature* 356, 74-76 (1992).
38. Tanenbaum, M. E. & Medema, R. H. Mechanisms of centrosome separation and bipolar spindle assembly. *Dev. Cell* 19, 797-806 (2010).
39. Tsou, M-F. B. et al. Polo kinase and separase regulate the mitotic licensing of centriole duplication in human cells. *Dev. Cell* 17, 344-354 (2009).
40. Marschall, L. G., Jeng, R. L., Mulholland, J. & Stearns, T. Analysis of Tub4p, a yeast γ-tubulin-like protein: implications for microtubule-organizing center function. *J. Cell Biol.* 134, 443-454 (1996).
41. Kobayashi, T., Tsang, W. Y., Li, J., Lane, W. & Dynlacht, B. D. Centriolar kinesin Kif24 interacts with CP110 to remodel microtubules and regulate ciliogenesis. Cell 145, 914-925 (2011).
42. Leisner, C. et al. Regulation of mitotic spindle asymmetry by SUMO and the spindle-assembly checkpoint in yeast. *Curr. Biol.* 18, 1249-1255 (2008).
43. Yamashita, Y. M. & Fuller, M. T. Asymmetric centrosome behavior and the mechanisms of stem cell division. *J. Cell Biol.* 180, 261-266 (2008).
44. Campbell, E. K. M., Werts, A. D. & Goldstein, B. A cell cycle timer for asymmetric spindle positioning. *PLoS Biol.* DOI: 10.1371/journal.pbio.1000088 (2009).
45. Caydasi, A. K., Ibrahim, B. & Pereira, G. Monitoring spindle orientation: spindle position checkpoint in charge. *Cell Division* 5, 1-15 (2010).
46. Hotz, M., Lengefeld, J. & Barral, Y. The MEN mediates the effects of the spindle assembly checkpoint on Kar9-

47. Johnson, A. E., McCollum, D. & Gould, K. L. Polar opposites: fine-tuning cytokinesis through SIN asymmetry. *Cytoskeleton* 69, 686-699 (2012).
48. Furuta, K., Edamatsu, M., Maeda, T., Toyoshima, Y. Y. Diffusion and directed movement: in vitro motile properties of fission yeast kinesin-14 Pkl1. *J. Biol. Chem.* 283, 36465-36473 (2008).
49. Craik, D. J., Fairlie, D. P., Liras, S. & Price, D. The future of peptide-based drugs. *Chem. Biol.* Drug Des. 81, 136-147 (2013).
50. Mayer, T. U. et al. Small molecule inhibitor of mitotic spindle bipolarity identified in a phenotype-based screen. *Science* 286, 971-974 (1999).
51. Chan, K-S. et al. Mitosis-targeted anti-cancer therapies: where they stand. *Cell Death Dis.* DOI: 10.1038/cddis.2012.148 (2012).
52. Katsetos, C. D. et al. Altered cellular distribution and subcellular sorting of ▢-tubulin in diffuse astrocytic gliomas and human glioblastoma cell lines. *J. Neuropathol. Exp. Neurol.* 65, 465-477 (2006).
53. Katsetos, C. D. et al. Class III β-tubulin and γ-tubulin are co-expressed and form complexes in human glioblastoma cells. *Neurochem. Res.* 32, 1387-1398 (2007).
54. Liu, T., Niu, Y., Yu, Y., Liu, Y. & Zhang, F. Increased ▢-tubulin expression and P16$^{INK4A}$ promoter methylation occur together in preinvasive lesions and carcinomas of the breast. *Ann Oncol.* 20 Martha Buntin, 441-448 (2009).
55. Niu, Y. et al. Increased expression of centrosomal a, γ-tubulin in atypical ductal hyperplasia and carcinoma of the breast. *Cancer Sci.* 100, 580-587 (2009).
56. Syed, M. I. et al. Gamma tubulin: A promising indicator of recurrence in squamous cell carcinoma of the larynx. *Otolaryngol. Head Neck Surg.* 140, 498-504 (2009).
57. Caracciolo, V. et al. Differential expression and cellular distribution of γ-tubulin and βIII-tubulin in medulloblastomas and human medulloblastoma cell lines. *J. Cell Physiol.* 223, 519-529 (2010).
58. Cho, E. H., Whipple, R. A., Matrone, M. A., Balzer, E. M. & Martin, S. S. Delocalization of γ-tubulin due to increased solubility in human breast cancer cell lines. *Cancer Biol. Ther.* 9, 66-76 (2010).
59. Loh, J-K. et al. Differential expression of centrosomal proteins at different stages of human glioma. *BMC Cancer* 10,268 (2010).
60. Maounis, N. F. et al. Overexpression of γ-tubulin in non-small cell lung cancer. *Histol. Histopathol.* 27, 1183-1194 (2012).
61. Rath, O. & Kozielski, F. Kinesins and Cancer. *Nat. Rev. Cancer* 12, 527-539 (2012).
62. Moreno, S., Klar, A. & Nurse, P. Molecular genetic analysis of fission yeast *Schizosaccharomyces pombe*. *Methods Enzymol.* 194, 795-823 (1991).
63. Maundrell, K. Thiamine-repressible expression vectors pRep and pRIP for fission yeast. *Gene* 123, 127-130 (1993).
64. Huang, Y., Hamada, M., Patel, J. & Maraia, R. J. Construction of FLAG and histidine tagging vectors for *Schizosaccharomyces pombe*. *Yeast* 18, 463-468 (2001).
65. Hou, H. et al. Csi1 links centromeres to the nuclear envelope for centromere clustering. *J. Cell Biol.* 199, 735-744 (2012).
66. Krawchuk, M. D. & Wahls, W. P. High-efficiency gene targeting in *Schizosaccharomyces pombe* using a modular, PCR-based approach with long tracts of flanking homology. *Yeast* 15, 1419-1427 (1999).
67. Woods, A. et al. Definition of individual components within the cytoskeleton of *Trypanosoma brucei* by a library of monoclonal antibodies. *J. Cell Sci.* 93, 491-500 (1989).
68. Samejima, I., Lourenco, P. C. C., Snaith, H. A. & Sawin, K. E. Fission yeast mto2p regulates microtubule nucleation by the centrosomin-related protein mto1p. *MBoC* 16, 3040-3051 (2005).
69. Burns, R. G. Analysis of the γ-tubulin sequences: implications for the functional properties of γ-tubulin. *J Cell Sci.* 108, 2123-2130 (1995).
70. Z. T. Olmsted, A. Colliver, T. D. Riehlman, and J. L. Paluh (2014) Kinesin-14 and kinesin-5 antagonistically regulate microtubule nucleation γ-TuRC in yeast and human cells. *Nature Communications* 5:5339. doi: 10.1038/ncomms 6339.

We claim:

1. A method for identifying a compound as a Kinesin-5 BimC antagonist, the method comprising culturing a eukaryotic cell transduced/transfected with a nucleic acid that encodes the peptide of SEQ ID NO: 1 in the presence and absence of said compound and monitoring the cell for mitotic arrest, wherein a compound that promotes mitotic arrest in the cell is identified as a Kinesin-5 BimC antagonist.

2. The method of claim 1, wherein said cell is cultured under conditions for cell growth.

3. The method of claim 1, where said cell is a yeast cell.

4. The method of claim 1, wherein said cell is a mammalian cell.

5. The method of claim 1, wherein said cell is a human breast cancer cell.

* * * * *